(12) United States Patent
Stossel et al.

(10) Patent No.: US 10,022,424 B2
(45) Date of Patent: Jul. 17, 2018

(54) USE OF GELSOLIN TO TREAT INFECTIONS

(75) Inventors: Thomas P. Stossel, Belmont, MA (US); Po-Shun Lee, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 259 days.

(21) Appl. No.: 11/129,670

(22) Filed: May 12, 2005

(65) Prior Publication Data
US 2006/0009386 A1  Jan. 12, 2006

Related U.S. Application Data

(60) Provisional application No. 60/570,233, filed on May 12, 2004.

(51) Int. Cl.
*A61K 39/00* (2006.01)
*A61K 38/17* (2006.01)

(52) U.S. Cl.
CPC ................................ *A61K 38/1709* (2013.01)

(58) Field of Classification Search
CPC ..... A61K 38/1709; A61K 38/00; A61K 31/00
USPC ............. 424/531, 530, 529; 514/2, 921, 1.1; 530/829, 830, 324, 350; 436/86; 435/69.6
See application file for complete search history.

(56) References Cited

U.S. PATENT DOCUMENTS

| | | |
|---|---|---|
| 5,071,773 A | 12/1991 | Evans et al. ................... 436/501 |
| 5,260,224 A | 11/1993 | Stossel et al. |
| 5,407,821 A | 4/1995 | Breakefield et al. ............. 435/6 |
| 5,464,817 A * | 11/1995 | Stossel ............... A61K 38/1709 424/94.1 |
| 5,508,265 A | 4/1996 | Stossel et al. |
| 5,569,588 A | 10/1996 | Ashby et al. ..................... 435/6 |
| 5,571,511 A | 11/1996 | Fischer |
| 5,580,265 A | 12/1996 | Koblitz et al. |
| 5,593,964 A * | 1/1997 | Goldstein et al. ............. 514/1.4 |
| 5,648,465 A * | 7/1997 | Margolis ............ G01N 33/6872 435/69.1 |
| 5,656,589 A * | 8/1997 | Stossel ............... A61K 38/1709 424/158.1 |
| 5,691,160 A * | 11/1997 | Janmey ............... A61K 38/1709 435/13 |
| 5,750,353 A | 5/1998 | Kopin et al. .................... 435/7.1 |
| 5,744,303 A | 6/1998 | Teng et al. ......................... 435/6 |
| 5,783,662 A | 7/1998 | Janmey et al. |
| 5,804,427 A | 9/1998 | Davis et al. |
| 5,830,436 A * | 11/1998 | Ghio et al. ....................... 424/45 |
| 5,846,743 A | 12/1998 | Janmey et al. |
| 5,925,529 A | 7/1999 | Coughlin et al. .............. 435/7.2 |
| 6,040,147 A | 3/2000 | Ridker et al. |
| 6,271,353 B1 * | 8/2001 | Nakamura ............. C07K 14/47 530/387.1 |
| 6,319,498 B1 | 11/2001 | Findeis et al. |
| 7,432,308 B2 | 10/2008 | Demeester et al. |
| 7,928,089 B2 * | 4/2011 | Morton et al. .................... 514/56 |
| 8,198,094 B2 | 6/2012 | Stossel et al. |
| 8,440,622 B2 | 5/2013 | Stossel et al. |
| 9,316,639 B2 * | 4/2016 | Stossel ................. G01N 33/564 |
| 9,408,891 B2 | 8/2016 | Janmey et al. |
| 9,575,072 B2 | 2/2017 | Thadhani et al. |
| 2002/0103112 A1 * | 8/2002 | Ferguson ........... A61K 38/1709 514/44 R |
| 2003/0083262 A1 * | 5/2003 | Hannig .................. A61K 38/08 514/1.7 |
| 2004/0072261 A1 | 4/2004 | Kostanjevecki et al. |
| 2004/0141961 A1 * | 7/2004 | Demeester et al. ........ 424/94.61 |
| 2006/0009386 A1 * | 1/2006 | Stossel et al. .................. 514/12 |
| 2007/0042432 A1 * | 2/2007 | Brown .......................... 435/7.2 |
| 2007/0087969 A1 | 4/2007 | Ferguson et al. |
| 2007/0238655 A1 * | 10/2007 | Bucki et al. .................... 514/12 |
| 2007/0238668 A1 * | 10/2007 | Janmey ............. A61K 38/1709 514/1.4 |
| 2008/0051348 A1 * | 2/2008 | Goldstein .............. A61K 38/16 514/2.8 |
| 2008/0125370 A1 | 5/2008 | Stossel et al. |
| 2008/0261260 A1 | 10/2008 | Stossel et al. |
| 2009/0053194 A1 * | 2/2009 | Goldstein ........ C07K 14/57581 424/130.1 |
| 2009/0258830 A1 | 10/2009 | Thadhani et al. |
| 2010/0021428 A1 | 1/2010 | Stossel et al. |
| 2010/0227807 A1 | 9/2010 | Stossel et al. |
| 2011/0144020 A1 * | 6/2011 | Goldstein .............. A61K 38/08 514/12.9 |

(Continued)

FOREIGN PATENT DOCUMENTS

| | | |
|---|---|---|
| CA | 2 142 121 A1 | 3/1994 |
| JP | H05-506034 A | 9/1993 |

(Continued)

OTHER PUBLICATIONS

Masover et al. J. Gen. Microbiol. 98: 587-593, 1977 (abstract only).*
Bucki et al. Antimicrob. Agents & Chemother. 48: 1526-1533, May 2004.*
Nollet et al. Vet. Microbiol. 65: 37-45, 1999.*
Zuo et al. Zhonhua Er Bi Yan Hou Jing Wai Ke Za Zhi 40: 524-527, Jul. 2005, English abstract.*
Rothenbach, PA et al, Joural of Applied Physiology, vol. 96, pp. 25-31, 2004, May 2, 2003, Recombinant plasma gelsolin infusion attenuates burn induced pulmonary microvascular dysfunction.*
Rochenbach, Patricia A. et al, J. Appl Physiol, vol. 96, pp. 25-31, 2004.*
Rogers et al., "Relationship of Gelsolin Levels to Outcomes in Critically Ill Patients", Journal of Surgical Research, vol. 107, No. 2, (Oct. 2002), (ISSN 0022-4804).

(Continued)

*Primary Examiner* — Albert M Navarro
(74) *Attorney, Agent, or Firm* — Wolf, Greenfield & Sacks, P.C.

(57) ABSTRACT

The invention relates to the use of gelsolin to treat infections and to monitor the treatment of infections. The invention also provides methods up-regulating interleukin expression and methods for down-regulating pro-inflammatory cytokine expression.

39 Claims, 8 Drawing Sheets

(56) References Cited

U.S. PATENT DOCUMENTS

| | | | | |
|---|---|---|---|---|
| 2012/0208743 A1* | 8/2012 | Stossel | ............ | G01N 33/564 514/1.7 |
| 2013/0230455 A1 | 9/2013 | Stossel et al. | | |
| 2015/0191695 A1 | 7/2015 | Song et al. | | |
| 2016/0228505 A1 | 8/2016 | Stossel et al. | | |
| 2017/0189483 A1 | 7/2017 | Thadhani et al. | | |

FOREIGN PATENT DOCUMENTS

| | | | | |
|---|---|---|---|---|
| JP | H08-500488 A | 1/1996 | | |
| JP | 2003-511356 A | 3/2003 | | |
| JP | 2004-532386 | 10/2004 | | |
| JP | 2004-534841 A | 11/2004 | | |
| JP | 2004-536786 A | 12/2004 | | |
| JP | 2005-041881 A | 2/2005 | | |
| JP | 2005-525998 A | 9/2005 | | |
| JP | 2007-524101 A | 8/2007 | | |
| JP | 2007-537292 A | 12/2007 | | |
| WO | 91/15770 | * | 10/1991 | ............ A61K 37/00 |
| WO | WO 91/15770 A1 | 10/1991 | | |
| WO | 91/17170 | * | 11/1991 | ............ A61K 37/22 |
| WO | WO 91/17170 A1 | 11/1991 | | |
| WO | WO 94/04704 A1 | 3/1994 | | |
| WO | 94/22465 | * | 10/1994 | ............ A61K 37/02 |
| WO | WO 94/22465 A1 | 10/1994 | | |
| WO | WO 95/09645 A1 | 4/1995 | | |
| WO | 95/24207 | * | 9/1995 | ............ A61K 38/00 |
| WO | 98/04589 | * | 2/1998 | ............ C07K 14/47 |
| WO | WO 0055350 | * | 9/2000 | |
| WO | WO 02/059604 A2 | 8/2002 | | |
| WO | WO 2002/059604 A2 | 8/2002 | | |
| WO | WO 02/070007 A1 | 9/2002 | | |
| WO | WO 03/006026 A1 | 1/2003 | | |
| WO | 03/020213 | * | 3/2003 | |
| WO | WO 03/020213 A2 | 3/2003 | | |
| WO | WO 2003/088811 A2 | 10/2003 | | |
| WO | WO 2004/023973 A2 | 3/2004 | | |
| WO | 2004/035008 | * | 4/2004 | |
| WO | WO 01/24828 A2 | 4/2004 | | |
| WO | WO 04/035008 A2 | 4/2004 | | |
| WO | WO 2004/082617 A2 | 9/2004 | | |
| WO | 2005/046454 | * | 5/2005 | |
| WO | WO 05/046454 A2 | 5/2005 | | |
| WO | WO 2005/085859 A1 | 9/2005 | | |
| WO | WO 05/112970 A2 | 12/2005 | | |
| WO | WO 2007/041245 A2 | 4/2007 | | |
| WO | WO 2007/106577 A2 | 9/2007 | | |
| WO | WO 2007/109056 A2 | 9/2007 | | |
| WO | WO 2009/094194 A2 | 7/2009 | | |
| WO | WO 2016/033187 A1 | 3/2016 | | |

OTHER PUBLICATIONS

Mounzer et al., "Relationship of Admission Plasma Gelsolin Levels to Clinical Outcomes in Patients after Major Trauma", Am J Respir Crit Care Med., vol. 160, (1999), pp. 1673-1681.
Lee et al., "Plasma Gelsolin Levels Predict the Outcomes of Critically Ill Patients in Surgical Intensive Care Unit", American Thoracic Society International Conference, A627, vol. 169, No. 7, Apr. 2004 (ATS 2004—Orlando).
Huang, "Temporal Association Between Serum Gelsolin Levels and Clinical Events in a Patient With Severe Falciaparum Malaria," (*Clinical Infectious Diseases* 1997; 24:951-4).
Janmey, "Phosphoinositide-Binding Peptides Derived From the Sequences of Gelsolin and Villin," (*Journal of Biological Chemistry* vol. 267, No. 17, Issue of Jun. 15, 1992, pp. 11818-11823).
Weiner, "The Antimicrobial Activity of the Cathelicidin LL37 Is Inhibited by F-actin Bundles and Restored by Gelsolin," (*Am. J. Respir. Cell Mol. Biol*. vol. 28, pp. 738-745, 2003).
International Search Report/Written Opinion from International Application No. PCT/US05/16798, dated Jan. 20, 2006.

Bannerman et al., "Increased Levels of LPS-Binding Protein in Bovine Blood and Milk Following Bacterial Lipopolysaccharide Challenge," J. Dairy Sci., vol. 86, pp. 3128-3137 (2003).
Becker et al., "The antimicrobial activity of the cathelicidin LL37 is inhibited by F-actin bundles and restored by gelsolin," *Amer. Journal of Respiratory Cell and Molecular Biology*, vol. 28, No. 4, (2003), pp. 478-484.
Berer et al., "Are the serum levels of endotoxin-binding proteins reliable predictors of complications in the course of peritonitis?," European Journal of Clinical Investigation, vol. 20, pp. 66-71 (1990).
Berger et al, "Evidence for endotoxin binding capacity of human Gc-globulin and transferrin," Clinica Chimica Acta, vol. 163, pp. 289-299 (1987).
Beutler et al, "Sepsis and evolution of the innate immune response," Crit Care Med, vol. 29, No. 7, pp. S2-S7 (2001).
Bowman et al., "Cultured Astrocytes Express Toll-Like Receptors for Bacterial Products," Glia, vol. 43, pp. 281-291 (2003).
Bsibsi et al., "Broad Expression of Toll-Like Receptors in the Human Central Nervous System," J Neuropathology Exp. Neurol.,vol. 61, No. 11, pp. 1013-1021 (2002).
Bosshart et al., Endotoxin-neutralizing effects of histidine-rich peptides, FEBS Letters, vol. 553, pp. 135-140 (2003).
Brandenburg et al., "Physicochemical properties of bacterial glycopolymers in relation to bioactivity," Carbohydrate Research, vol. 338, pp. 2477-2489 (2003).
Casas et al., "Reconstituted High-Density Lipoprotein Reduces LPS-Stimulated TNF," J. Sur. Res., vol. 59, pp. 544-552 (1995).
Christofidou-Solomidou et al., "Changes in plasma gelsolin concentration during acute oxidant lung injury in mice," *Lung*, vol. 180, No. 2, (2002) pp. 91-104.
Christofidou-Solomidou et al., "Recombinant Plasma Gelsolin Diminishes the Acute Inflammatory Response to Hyperoxia in Mice," J. Invest. Med., vol. 50, No. 1, pp. 54-60 (2002).
Cunningham et al, "Cell Permeant Polyphosphoinostide-binding Peptides that Block Cell Motility and Actin Assembly," J. Biol. Chem., vol. 276, pp. 43390-43399 (2001).
Dahl et al., "Plasma concentration of Gc-globulin is associated with organ dysfunction and sepsis after injury," Crit. Care Med, vol. 31, No. 1, pp. 152-156 (2003).
Dahl et al, "Plasma Gelsolin is Reduced in Trauma Patients," Shock, vol. 12, pp. 102-104 (1999).
Dahl et al., "Serum Gc-globulin in the early course of multiple trauma," Crit. Care Med., vol. 26, No. 2, pp. 285-289 (1998).
DiNubile et al, "Prognostic implications of declining plasma gelsolin levels after allogeneic stem cell transplantation," Blood, vol. 100, No. 13, pp. 4367-4371 (2002).
Erridge et al., "Structure and function of lipopolysaccharides," Microbes Infect., vol. 4, No. 8, pp. 837-851 (2002).
Faure et al., "Bacterial Lipopolysaccharide Activates NF-kB through Toll-like Receptor 4 (TLR-4) in Cultured Human Derman Endothelial Cells," J. Biol. Chem., vol. 275, No. 15, pp. 11058-11063 (2000).
Flanagan et al., "The S tructure of Divalent Cation-Induced Aggregates of PIP2 and their Alteration of Gelsolin and Tau," Biophysical Journal, vol. 73, pp. 1440-1447 (1997).
Ginsburg, "Role of lipoteichoic acid in infection and inflammation," Lancet Infect. Diseases, vol. 2, pp. 171-179 (2002).
Goetzl et al., "Gelsolin Binding and Cellular Presentation of Lysophosphatidic Acid," J. Biol. Chem., vol. 275, No. 19, pp. 14573-14578 (2000).
Goldschmidt-Clermont et al., "Role of Group-specific Component (Vitamin D Binding Protein) in Clearance of Actin from the Circulation in the Rabbit," J. Clin. Invest., vol. 81, pp. 1519-1527 (1988).
Gutsmann et al., "Dual Role of Lipopolysacharide (LPS)-Binding Protein in Neutralization of LS and Enhancement of LPS-Induced Activation of Mononuclear Cells," Infect. and Immun., vol. 69, No. 11, pp. 6942-6950 (2001).
Harris et al., "Lipoprotein-bound LPS induces cytokine tolerance in hepatocytes," J. of Endotoxin Res., vol. 9, pp. 45-50 (2003).
Hattar et al., "Lipoteichoic acid (LTA) from *Staphylococcus aureus* stimulates human neutrophil cytokine release by a CD14-depen-

(56) References Cited

OTHER PUBLICATIONS dent, Toll-like-receptor-independent mechanism: Autocrine role of tumor necrosis factor-a in mediating LTA-induced interleukin-8 generation," Crit. Care Med., vol. 34, pp. 835-841 (2006).
Hayter et al., "Neutron Scattering Analysis of Bacterial Lipopolysaccharide Phase Structure," J. Biol. Chem., vol. 262, pp. 5100-5105 (1987).
Hummell et al., "Bacterial Lipoteichoic Acid Sensitizes Host Cells for Destruction by Autologous Complement," J. Clin. Invest., vol. 77, No. 5, pp. 1533-1538 (1986).
Igarashi et al., "Sphingosine-Phosphate Content in the Plasma of Platelet Concentrates Correlates with Poor Platelet Increments after Transfusion and with occurrences of Transfusion Reactions in Patients," Am. J. Hematol., vol. 57, pp. 261-262 (1998).
Jammey et al., Modulation of gelsolin function by phosphatidylinositol 4,5-bisphosphate, Nature, vol. 325, pp. 362-364 (1987).
Jammey et al., "Interactions of Gelsolin and Gelsolin-Actin Complexes with Actin. Effects of Calcium on Actin Nucleation, Filament Severing, and End Blocking," Biochemistry, vol. 24, pp. 3714-3723 (1985).
Jammey et al., "Polyphosphoinositide Micelles and Polyphosphoinositide-containing Vesicles Dissociate Endogenous Gelsolin-Actin Complexes and Promote Actin Assembly from the Fast-growing End of Actin Filaments Blocked by Gelsolin," J. Biol. Chem., vol. 262, pp. 12228-12236 (1987).
Jammey et al., "Capacity of Human Serum to Depolymerize Actin Filaments," Blood, vol. 70, pp. 524-530 (1987).
Jammey et al., "Deconstructing gelsolin: identifying sites that mimic or alter binding to actin and phosphoinositides," Chem. Biol., vol. 5, pp. R81-R85 (1998).
Jorgensen et al., "Peptidoglycan and Lipoteichoic Acid Modify Monocyte Phenotype in Human Whole Blood," Clin. Diagn. Lab. Immunol., vol. 8, pp. 515-521 (2001).
Kawamura et al., "Lipoteichoic Acid-Induced Neutrophil Adhesion via E-Selectin to Human Umbilical Vein Endothelial Cells (HUVECs)," Biochem. Biophys. Res. Commun., vol. 217, pp. 1208-1215 (1995).
Kouyama et al., "Fluorimetry Study of N-(1-Pyrenyl)iodoacetamide-Labelled F-Actin," Eur. J. Biochem., vol. 114, pp. 33-38 (1981).
Kwiatkowski et al., "Plasma and cytoplasmic gelsolins are encoded by a single gene and contain a duplicated actin-binding domain," Nature, vol. 323, pp. 455-458 (1986).
Kwiatkowski et al., "Functions of gelsolin: motility, signaling, apoptosis, cancer," Curr. Opin. Cell Biol., vol. 11, pp. 103-108 (1999).
Kwiatkowski et al., "Muscle is the Major Source of Plasma Gelsolin," J. Biol. Chem., vol. 263, pp. 8239-8243 (1988).
Lee et al., "The Extracellular Actin-Scavenger System and Actin Toxicity," N. Engl. J. Med., vol. 326, pp. 1335-1341 (1992).
Lee et al., "Relationship of Plasma Gelsolin Levels to Outcomes in Critically Ill Surgical Patients," *Annals of Surgery*, vol. 243, No. 3, pp. 399-403 (2006).
Li et al., "The critical micelle concentrations of Lysophosphatidic acid and sphingosylphosphorylcholine," Chem. Phys. Lipids, vol. 130, pp. 197-201 (2004).
Liepina et al., "Molecular Dynamics Study of a Gelsolin-Derived Peptide Binding to a Lipid Bilayer Containing Phosphatidylinositol 4,5-Bisphosphate," Biopolymers, vol. 71, pp. 49-70 (2003).
Lind et al., "Role of Plasma Gelsolin and the Vitamin D-binding Protein in Clearing Actin from the Circulation," J. Clin. Invest., vol. 78, pp. 736-742 (1986).
Masover et al., "The effect of growth and urea concentration on ammonia production by a urea-hydrolysing mycoplasma (Ureaplasma urealyticum," J. Gen. Microbiol., vol. 98, pp. 587-593 (1977).
Mathison et al., "Plasma Lipopolysaccharide (LPS)-Binding Protein, A Key Component in Macrophage Recognition of Gram-Negative LPS," J. Immun., vol. 149, pp. 200-206 (1992).

Meerschaert et al., "Gelsolin and functionally similar actin-binding proteins are regulated by lysophosphatidic acid," EMBO Journal, vol. 17, pp. 5923-5932 (1998).
Mertsola et al., "Release of endotoxin after antibiotic treatment of Gram-negative bacterial meningitis," Ped. Inf. Dis. J., vol. 8, pp. 904-906 (1989).
Mintzer et al., "Lysophosphatidic acid and lipopolysaccharide bind to the PIP2-binding domain of gelsolin," Biochem. Biophysic. Acta, vol. 1758, pp. 85-98 (2006).
Nugent et al., "Sphingosine-1-phosphate: characterization of its inhibition of platelet aggregation," Platelets, vol. 11, pp. 226-232 (2000).
Overland et al., "Lipoteichoic Acid is a Potent Inducer of Cytokine Production in Rat and Human Kupffer Cells in Vitro," Sur. Infect., vol. 4, No. 2, pp. 181-189 (2003).
Riedermann et al., "The enigma of sepsis," J. Clin. Invest., vol. 112, pp. 460-467 (2003).
Rothenbach et al., "Recombinant plasma gelsolin infusion attenuates burn-induced pulmonary microvascular dysfunction," J. Appl. Physiol., vol. 96, pp. 25-31 (2004).
Rustici et al., "Molecular Mapping and Detoxification of the Lipid a Binding Site by Synthetic Peptides," Science, vol. 259, pp. 361-365 (1993).
Salat et al., "The Relevance of Plasminogen Activator Inhibitor 1 (PAI-1) as a Marker for the Diagnosis of Hepatic Veno-Occlusive Disease in Patients after Bone Marrow Transplantation," Leukemia and Lymphoma, vol. 33, pp. 25-32 (1999).
Saura et al., "Microglial apolipoprotein E and astroglial apolipoprotein J expression in vitro: opposite effects of lipopolysaccharide," J. Neurochem. vol. 85, pp. 1455-1467 (2003).
Scarborough et al., "Aggregation of Platelets by Muscle Actin. A Multivalent Interaction Model of Platelet Aggregation by ADP," Biochem. Biophys. Res. Comm., vol. 100, pp. 1314-1319 (1981).
Schroder et al., "Lipoteichoic Acid (LTA) of *Streptococcus pneumoniae* and *Staphylococcus aureus* Activates Immune Cells via Toll-like Receptor (TLR)-2, Lipopolysaccharide-binding Protein (LBP), and CD14, whereas TLR-4 and MD-2 Are Not Involved," J. Biol. Chem. vol. 278, pp. 15587-15594 (2003).
Schultz et al., "Animal and human models for sepsis," Ann. Med., vol. 34, pp. 573-581 (2002).
Sheu et al., "Mechanisms involved in the antiplatelet activity of *Escherichia coli* lipopolysaccharide in human platelets," Br. J. Haemat., vol. 103, pp. 29-38 (1998).
Shimazu et al., "MD-2, a Molecule that Confers Lipopolysaccharide Responsiveness on Toll-like Receptor 4," J. Exp. Med., vol. 189, pp. 1777-1782 (1999).
Smith et al., "Decreased Plasma Gelsolin Levels in Patients with Plasmodium falciparum Malaria: A Consequence of Hemolysis?" Blood, vol. 72, pp. 214-218 (1988).
Spudich et al., "The Regulation of Rabbit Skeletal Muscle Contraction, I. Biochemical studies of the interaction of the tropomyosin-troponin complex with actin and the proteolytic fragments of myosin," J. Biol. Chem., vol. 246, pp. 4866-4871 (1971).
Stossel, Thomas P., "From Signal to Pseudopod, How Cells Control Cytoplasmic Actin Assembly," J. Biol. Chem., vol. 264, pp. 18261-18264 (1989).
Suhler et al., "Decreased plasma gelsolin concentrations in acute liver failure, myocardial infarction, septic shock, and myonecrosis," Crit. Care Med., vol. 25, pp. 594-598 (1997).
Sun et al., "Gelsolin, a Multifunctional Actin Regulatory Protein," J. Biol. Chem., vol. 274, pp. 33179-33182 (1999).
Tauber et al., "Antibiotic therapy, Endotoxin Concentration in Cerebrospinal Fluid, and Brain Edema in Experimental *Escherichia coli* Meningitis in Rabbits," J. Infect. Diseases, vol. 156, pp. 456-462 (1987).
Thomas et al., "Biopanning of endotoxin-specific phage displayed peptides," Biochem. and Biophys. Res. Comm., vol. 307, pp. 133-138 (2003).
Tobias et al., "Control of Lipopolysaccharide-High-Density Lipoprotein Interactions by an Acute-Phase Reactant in Human Serum," Infection and Immun., vol. 50, pp. 73-76 (1985).

(56) References Cited

OTHER PUBLICATIONS

Tobias et al., "Isolation of a lipopolysaccharide-binding acute phase reactant from rabbit serum," J. Exp. Med., vol. 164, pp. 777-793 (1986).
Tuominen et al., "Fluorescent phosphoinositide derivatives reveal specific binding of gelsolin and other actin regulatory proteins to mixed lipid bilayers," Eur. J. Biochem., vol. 263, pp. 85-92 (1999).
Van Oosten et al., "Scavenger receptor-like receptors for the binding of lipopolysaccharide and lipoteichoic acid to liver endothelial and Kupffer cells," J. Endotoxin Res., vol. 7, pp. 381-384 (2001).
Villa et al., "Pattern of Cytokines and Pharmacomodulation in Sepsis Induced by Cecal Ligation and Puncture Compared with that Induced by Endotoxin," Clin. Diag. Lab. Immun., vol. 2, pp. 549-553 (1995).
Vreugdenhil et al., "Lipopolysaccharide (LPS)-Binding Protein Mediates LPS Detoxification by Chylomicrons," J. Immun., vol. 170, pp. 1399-1405 (2003).
Wang et al., "HMG-1 as a Late Mediator of Endotoxin Lethality in Mice," Science, vol. 285, pp. 157-288 (1999).
Ware et al., "The Acute Respiratory Distress Syndrome," N. Engl. J. Med., vol. 342, pp. 1334-1349 (2000).
Watson et al., "Genetic Control of Responses to Bacterial Lipopolysaccharides in Mice, II. A Gene that Influences a Membrane Component Involved in the Activation of Bone Marrow-derived Lymphocytes by Lipopolysaccharides," J. Immun., vol. 114, pp. 1462-1468 (1975).
Wen et al., "The Plasma and Cytoplasmic Forms of Human Gelsolin Differ in Disulfide Structure," Biochemistry, vol. 35, pp. 9700-9709 (1996).
Yamamura et al., "Sphingosine-1-phosphate inhibits actin nucleation and pseudopodium formation to control cell motility of mouse melanoma cells," FEBS Letters, vol. 382, pp. 193-197 (1996).
Yatomi, Y., "Sphingosine 1-Phosphate in Vascular Biology: Possible Therapeutic Strategies to Control Vascular Diseases," Current Pharma. Design, vol. 12, pp. 575-587, (2006).
Angus et al., "Epidemiology of sepsis: An update," *Crit. Care. Med.*, vol. 29, No. 78 (Suppl.) 2001, pp. S109-S116.
Yancey et al, "Risk Factors for Neonatal Sepsis," *Obstetrics & Gynecology*, vol. 87, No. 2, 1996, pp. 188-194.
Moss, M., "Epidemiology of Sepsis: Race, Sex, and Chronic Alcohol Abuse," Supplement Article, Clinical infectious diseases: an official publication of the Infectious Diseases Society of America), vol. 41, Suppl. 7, 2005, pp. S490-S497.
Overhaus, M. et al. "Mechanisms of polymicrobial sepsis-induced ileus" AM J Physiol Gastrointest Liver Physiol 287: G685-G694, 2004.
Lee, P. et al. "Plasma gelsolin is a marker and therapeutic agent in animal sepsis" Crit Care Med, vol. 35, No. 3: 849-855, 2007.
EP 10185573.2, dated Apr. 1, 2011, Partial European Search Report.
PCT/US2005/016798, dated Nov. 18, 2005, Invitation to Pay Additional Fees.
PCT/US2005/016798, dated Nov. 23, 2006, International Preliminary Report on Patentability.
EP 07753226.5, dated Feb. 17, 2009, Extended European Search Report.
PCT/US2007/006581, dated Aug. 11, 2008, International Search Report and Written Opinion.
PCT/US2007/006581, dated Sep. 25, 2008, International Preliminary Report on Patentability.
EP 07753102.8, dated Jun. 10, 2009, Extended European Search Report.
PCT/US2007/006451, dated Sep. 25, 2007, International Search Report and Written Opinion.
PCT/US2007/006451, dated Sep. 25, 2008, International Preliminary Report on Patentability.
EP 04810817.9, dated Jun. 10, 2010, Supplemental European Search Report.
PCT/US2004/037763, dated May 5, 2005, Invitation to Pay Additional Fees.
PCT/US2004/037763, dated Aug. 31, 2005, International Search Report and Written Opinion.
PCT/US2004/037763, dated May 26, 2006, International Preliminary Report on Patentability.
EP 09703176.9, dated Jan. 17, 2011, Extended European Search Report.
PCT/US2009/000452, dated Mar. 16, 2009, Invitation to Pay Additional Fees.
PCT/US2009/000452, dated May 18, 2009, International Search Report and Written Opinion.
PCT/US2009/000452, dated Aug. 5, 2010, International Preliminary Report on Patentability.
Office Communication dated Jun. 30, 2009 for U.S. Appl. No. 12/026,761.
Office Communication dated Mar. 12, 2010 for U.S. Appl. No. 12/026,761.
Partial European Search Report for EP 10185573.2 dated Apr. 1, 2011.
Invitation to Pay Additional Fees for PCT/US2005/016798 dated Nov. 18, 2005.
International Preliminary Report on Patentability for PCT/US2005/016798 dated Nov. 23, 2006.
Extended European Search Report for EP 07753226.5 dated Feb. 17, 2009.
International Search Report and Written Opinion for PCT/US2007/006581 dated Aug. 11, 2008.
International Preliminary Report on Patentability for PCT/US2007/006581 dated Sep. 25, 2008.
Extended European Search Report for EP 07753102.8 dated Jun. 10, 2009.
International Search Report and Written Opinion for PCT/US2007/006451 dated Sep. 25, 2007.
International Preliminary Report on Patentability for PCT/US2007/006451 dated Sep. 25, 2008.
Supplemental European Search Report for EP 04810817.9 dated Jun. 10, 2010.
Invitation to Pay Additional Fees for PCT/US2004/037763 dated May 5, 2005.
International Search Report and Written Opinion for PCT/US2004/037763 dated Aug. 31, 2005.
International Preliminary Report on Patentability for PCT/US2004/037763 dated May 26, 2006.
Extended European Search Report for EP 09703176.9 dated Jan. 17, 2011.
Invitation to Pay Additional Fees for PCT/US2009/000452 dated Mar. 16, 2009.
International Search Report and Written Opinion for PCT/US2009/000452 dated May 18, 2009.
International Preliminary Report on Patentability for PCT/US2009/000452 dated Aug. 5, 2010.
Genbank Submission; NIH/NCBI, Accession No. 1211330A; Kwiatkowski et al.; Oct. 1, 1996. Last accessed Feb. 3, 2005 at. 2 pages.
Genbank Submission; NIH/NCBI, Accession No. CAA28000; Kwiatkowski et al.; Mar. 21, 1995. Last accessed Feb. 3, 2005 at 2 pages.
Genbank Submission; NIH/NCBI, Accession No. X04412.1; Kwiatkowski et al.; Oct. 7, 2008, one page.
[No Author Listed] "Risk". Dorlands Medical Dictionary. Merck Source. Last accessed on Jun. 29, 2009 available at 2009. 2 pages.
[No Author Listed] "Risk". Medical Dictionary. Last accessed on Jun. 29, 2009 available at 2009. 1 page.
[No Author Listed] "Risk". Rogets II the New Thesaurus NY, Expanded Edition. Houghton Mifflin Company. New York 1988:843.
Adams et al., Fibrin mechanisms and functions in nervous system pathology. Mol Interv. Jun. 2004;4(3):163-76.
Aidinis et al., Cytoskeletal rearrangements in synovial fibroblasts as a novel pathophysiological determinant of modeled rheumatoid arthritis. PLoS Genet. Oct. 2005;1(4):e48. Epub Oct. 28, 2005. 12 pages.

(56) References Cited

OTHER PUBLICATIONS

Barnard et al., Targeted deletion of gelsolin potentiates endotoxin-induced murine lung vascular leak. FASEB. 2004;18(4-5):A352. Abstract 233.8.

Beddhu et al., Inflammation and inverse associations of body mass index and serum creatinine with mortality in hemodialysis patients. J Ren Nutr. Nov. 2007;17(6):372-80.

Bochicchio et al., Reclassification of urinary tract infections in critically ill trauma patients: a time-dependent analysis. Surg Infect (Larchmt). 2003 Winter;4(4):379-85. Abstract only.

Bucki et al., Bacterial endotoxin as inhibitor of the enzymatic activity of human thrombin. Eur J Haematol. Jun. 2006;76(6):510-5. Epub Mar. 9, 2006.

Bucki et al., Extracellular gelsolin binds lipoteichoic acid and modulates cellular response to proinflammatory bacterial wall components. J Immunol. Oct. 1, 2008;181(7):4936-44.

Bucki et al., Inactivation of endotoxin by human plasma gelsolin. Biochemistry. Jul. 19, 2005;44(28):9590-7.

Candiano et al., Gelsolin secretion in interleukin-4-treated bronchial epithelia and in asthmatic airways. Am J Respir Crit Care Med. Nov. 1, 2005;172(9):1090-6. Epub Aug. 11, 2005.

Chauhan et al., Binding of gelsolin, a secretory protein, to amyloid beta-protein. Biochem Biophys Res Commun. May 10, 1999;258(2):241-6.

Cirioni et al., Potential therapeutic role of histatin derivative P-113d in experimental rat models of Pseudomonas aeruginosa sepsis. J Infect Dis. Jul. 15, 2004;190(2):356-64. Epub Jun. 21, 2004.

Cohen et al., Therapeutic potential of plasma gelsolin administration in a rat model of sepsis. Cytokine. Jun. 2011;54(3):235-8. Epub Mar. 21, 2011.

Dinubile et al., Decreased gelsolin levels are associated with interstitial pneumonia after allogenic BMT. Blood. 1998;92(Suppl):683a. Abstract 2814.

Erukhimov et al., Actin-containing sera from patients with adult respiratory distress syndrome are toxic to sheep pulmonary endothelial cells. Am J Respir Crit Care Med. Jul. 2000;162(1):288-94.

Fouque et al., A proposed nomenclature and diagnostic criteria for protein-energy wasting in acute and chronic kidney disease. Kidney Int. Feb. 2008;73(4):391-8. Epub Dec. 19, 2007.

Goetzl, Pleiotypic mechanisms of cellular responses to biologically active lysophospholipids. Prostaglandins. Apr. 2001;64(1-4):11-20.

Güntert et al., Plasma gelsolin is decreased and correlates with rate of decline in Alzheimer's disease. J Alzheimers Dis. 2010;21(2):585-96. Abstract only.

Haddad et al., Angiopathic consequences of saturating the plasma scavenger system for actin. Proc Natl Acad Sci U S A. Feb. 1990;87(4):1381-5.

Hartung et al., Inflammatory mediators in demyelinating disorders of the CNS and PNS. J Neuroimmunol. Oct. 1992;40(2-3):197-210.

Himmelfarb et al., The elephant in uremia: oxidant stress as a unifying concept of cardiovascular disease in uremia. Kidney Int. Nov. 2002;62(5):1524-38.

Hsueh et al., Hypertension, the endothelial cell, and the vascular complications of diabetes mellitus. Hypertension. Aug. 1992;20(2):253-63.

Hyde et al., Mortality and bacteriology of sepsis following cecal ligation and puncture in aged mice. Infect Immun. Mar. 1990;58(3):619-24.

Ito et al., Depression of plasma gelsolin level during acute liver injury. Gastroenterology. May 1992;102(5):1686-92.

Janmey et al., Functional comparison of villin and gelsolin. Effects of Ca2+, KCl, and polyphosphoinositides. J Biol Chem. Nov. 15, 1988;263(32):16738-43.

Jensen et al., Features of endothelial dysfunction in early diabetic nephropathy. Lancet. Mar. 4, 1989;1(8636):461-3.

Jordan et al., Gelsolin is depleted in post-shock mesenteric lymph. J Surg Res. Nvo. 2007;143(1):130-5. doi: 10.1016/j.jss.2007.04.017.

Kalantar-Zadeh et al., A malnutrition-inflammation score is correlated with morbidity and mortality in maintenance hemodialysis patients. Am J Kidney Dis. Dec. 2001;38(6):1251-63.

Kalantar-Zadeh et al., Effect of malnutrition-inflammation complex syndrome on EPO hyporesponsiveness in maintenance hemodialysis patients. Am J Kidney Dis. Oct. 2003;42(4):761-73.

Kaysen et al., Longitudinal and cross-sectional effects of C-reactive protein, equilibrated normalized protein catabolic rate, and serum bicarbonate on creatinine and albumin levels in dialysis patients. Am J Kidney Dis. Dec. 2003;42(6):1200-11.

Kent et al., A monoclonal antibody to alpha 4 integrin suppresses and reverses active experimental allergic encephalomyelitis. J Neuroimmunol. Apr. 1995;58(1):1-10.

Kulakowska et al., Gelsolin concentration in cerebrospinal fluid from patients with multiple sclerosis and other neurological disorders. Eur J Neurol. Jun. 2008;15(6):584-8.

Kulakowska et al., Hypogelsolinemia, a disorder of the extracellular actin scavenger system, in patients with multiple sclerosis. BMC Neurol. Nov. 1, 2010;10:107. 8 pages.

Kwiatkowski et al., Identification of critical functional and regulatory domains in gelsolin. J Cell Biol. May 1989;108(5):1717-26.

Kwiatkowski et al., Isolation and properties of two actin-binding domains in gelsolin. J Biol Chem. Dec. 5, 1985;260(28):15232-8.

Lazarus et al., Role of bioincompatibility in dialysis morbidity and mortality. Am J Kidney Dis. Dec. 1994;24(6):1019-32.

Lee et al., Plasma gelsolin and circulating actin correlate with hemodialysis mortality. J Am Soc Nephrol. May 2009;20(5):1140-8. Epub Apr. 23, 2009.

Lee et al., Plasma Gelsolin Depletion and Circulating Actin in Sepsis: A Pilot Study. PLoS One. 2008;3(11):e3712. doi:10.1371/journal.pone.0003712. 5 pages.

Lee et al., Plasma Gelsolin Is a Critical Pro-Survival Factor in Sepsis. American Thoracic Society. 2005. Last accessed Feb. 15, 2012 at http://www.mindcull.com/data/american-thoracic-society/ats-2005-american-thoracic-soci . . . Abstract only. 1 page.

Lee et al., The potential role of plasma gelsolin in dialysis-related protein-energy wasting. Blood Purif. 2010;29(2):99-101. Epub Jan. 8, 2010.

Lind et al., Depression of gelsolin levels and detection of gelsolin-actin complexes in plasma of patients with acute lung injury. Am Rev Respir Dis. Aug. 1988;138(2):429-34.

Lind et al., Human plasma gelsolin binds to fibronectin. J Biol Chem. Nov. 10, 1984;259(21):13262-6.

Löfberg et al., Serum gelsolin and rhabdomyolysis. J Neurol Sci. May 7, 1998;157(2):187-90.

Matsumoto et al., Diagnosis of sepsis based on the host response. The Official Journal of Japanese Society of Laboratory Medicine. 1999;47(6):494-500. Japanese language reference.

Matsuoka et al., Novel therapeutic approach for the treatment of Alzheimer's disease by peripheral administration of agents with an affinity to beta-amyloid. J Neurosci. Jan. 1, 2003;23(1):29-33.

Maury, Homozygous familial amyloidosis, Finnish type: demonstration of glomerular gelsolin-derived amyloid and non-amyloid tubular gelsolin. Clin Nephrol. Jul. 1993;40(1):53-6. Abstract only.

McIntyre et al., Patients receiving maintenance dialysis have more severe functionally significant skeletal muscle wasting than patients with dialysis-independent chronic kidney disease. Nephrol Dial Transplant. Aug. 2006;21(8):2210-6. Epub Feb. 27, 2006.

Mezzano et al., Endothelial cell markers in chronic uremia: relationship with hemostatic defects and severity of renal failure. Thromb Res. Dec. 15, 1997;88(6):465-72.

Mezzano et al., Inflammation, not hyperhomocysteinemia, is related to oxidative stress and hemostatic and endothelial dysfunction in uremia. Kidney Int. Nov. 2001;60(5):1844-50.

Mitch et al., Mechanisms of muscle wasting. The role of the ubiquitin-proteasome pathway. N Engl J Med. Dec. 19, 1996;335(25):1897-905.

Morgan, Risk factors for infection in the trauma patient. J Natl Med Assoc. Dec. 1992;84(12):1019-23.

Myers et al., Collagen-induced arthritis, an animal model of autoimmunity. Life Sci. 1997;61(19):1861-78.

Nandakumar et al., Efficient promotion of collagen antibody induced arthritis (CAIA) using four monoclonal antibodies specific

(56) References Cited

OTHER PUBLICATIONS for the major epitopes recognized in both collagen induced arthritis and rheumatoid arthritis. J Immunol Methods. Sep. 2005;304(1-2):126-36.
Ni et al., The ubiquitin-proteasome pathway mediates gelsolin protein downregulation in pancreatic cancer. Mol Med. Sep.-Oct. 2008;14(9-10):582-9.
Osborn et al., Decreased levels of the gelsolin plasma isoform in patients with rheumatoid arthritis. Arthritis Res Ther. 2008;10(5):R117. Epub Sep. 27, 2008. 9 pages.
Osborn et al., Modifications of cellular responses to lysophosphatidic acid and platelet-activating factor by plasma gelsolin. Am J Physiol Cell Physiol. Apr. 2007;292(4):C1323-30. Epub Nov. 29, 2006.
Otero-Antón et al. Cecal ligation and puncture as a model of sepsis in the rat: influence of the puncture size on mortality, bacteremia, endotoxemia and tumor necrosis factor alpha levels. Eur Surg Res. 2001;33(2):77-9.
Owen et al., The urea reduction ratio and serum albumin concentration as predictors of mortality in patients undergoing hemodialysis. N Engl J Med. Sep. 30, 1993;329(14):1001-6.
Semba et al., Low serum selenium is associated with anemia among older adults in the United States. Eur J Clin Nutr. Jan. 2009;63(1):93-9. Published online Sep. 5, 2007. doi: 10.1038/sj.ejcn.1602889.
Smith et al., Evidence for two pathways of protein kinase C induction of 2ar expression: correlation with mitogenesis. J Cell Physiol. Apr. 1989;139(1):189-95.
Smith et al., Quantitative measurement of plasma gelsolin and its incorporation into fibrin clots. J Lab Clin Med. Aug. 1987;110(2):189-95.
Trautner et al., Role of biofilm in catheter-associated urinary tract infection. Am J Infect Control. May 2004;32(3):177-83. doi: 10.1016/j.ajic.2003.08.005.
Visapää et al., Correlation of Ki-67 and gelsolin expression to clinical outcome in renal clear cell carcinoma. Urology. Apr. 2003;61(4):845-50.
Walker et al., Enhanced Pseudomonas aeruginosa biofilm development mediated by human neutrophils. Infect Immun. Jun. 2005;73(6):3693-701.
Wanner et al., Atorvastatin in patients with type 2 diabetes mellitus undergoing hemodialysis. N Engl J Med. Jul. 21, 2005;353(3):238-48.
Witke et al., Hemostatic, inflammatory, and fibroblast responses are blunted in mice lacking gelsolin. Cell. Apr. 7, 1995;81(1):41-51.
Workeneh et al., Review of muscle wasting associated with chronic kidney disease. Am J Clin Nutr. Apr. 2010;91(4):1128S-1132S. Epub Feb. 24, 2010.
Yamamoto et al., Human plasma gelsolin binds adenosine triphosphate. J Biochem. Oct. 1990;108(4):505-6.
Yin et al., Structure and biosynthesis of cytoplasmic and secreted variants of gelsolin. J Biol Chem. Apr. 25, 1984;259(8):5271-6.
[No Author Listed] Choice of Control Group and Related Issues in Clinical Trials, E10. ICH Harmonised Tripartite Guideline. International Conference on Harmonisation of Technical Requirements for Registration of Pharmaceuticals for Human Use. Jul. 20, 2000. 35 pages.
[No Author Listed] E10 Choice of Control Group and Related Issues in Clinical Trials. Guidance for Industry. U.S. Department of Health and Human Services, Food and Drug Administration, Center for Drug Evaluation and Research (CDER), and Center for Biologics Evaluation and Research (CBER). May 2001. 37 pages.
[No Author Listed] Pharmacokinetics in Patients with Impaired Hepatic Function: Study Design, Data Analysis, and Impact on Dosing and Labeling. Guidance for Industry. U.S. Department of Health and Human Services, Food and Drug Administration, Center for Drug Evaluation and Research (CDER), and Center for Biologics Evaluation and Research (CBER). May 2003. 19 pages.

Badid et al., Role of myofibroblasts during normal tissue repair and excessive scarring: interest of their assessment in nephropathies. Histol Histopathol. Jan. 2000;15(1):269-80.
Brettschneider et al., Tau protein level in cerebrospinal fluid is increased in patients with early multiple sclerosis. Mult Scler. Jun. 2005;11(3):261-5.
Bucki et al., Plasma gelsolin: function, prognostic value, and potential therapeutic use. Curr Protein Pept Sci. Dec. 2008;9(6):541-51.
Chavko et al., Lung injury and recovery after exposure to blast overpressure. J Trauma. Oct. 2006;61(4):933-42.
Chebotareva et al., [The role of smooth muscle alpha-actin in development of renal fibrosis in patients with chronic glomerulonephritis]. Ter Arkh. 2006;78(5):17-21.
Chen, Multiple Sclerosis. Chinese Medicine Press. Jun. 30, 2000;67-73.
Dou, Immunocytology and Disease. Chapter 11. Chinese Medical Science and Technology Press. Sep. 30, 2004;404-415.
Grant et al., Reversal of Paralysis and Reduced Inflammation from Peripheral Administration of Amyloid-β in Th1- and Th17-Versions of Experimental Autoimmune Encephalomyelitis. Sci Transl Med. Aug. 1, 2012; 4(145): 145ra105.
Ji et al., Gelsolin levels are increased in the brain as a function of age during normal development in children that are further increased in Down syndrome. Alzheimer Dis Assoc Disord. Oct.-Dec. 2009;23(4):319-22.
Kulakowska et al., Depletion of plasma gelsolin in patients with tick-borne encephalitis and Lyme neuroborreliosis. Neurodegener Dis. 2011;8(5):375-80.
Liao et al., Overexpression of gelsolin in human cervical carcinoma and its clinicopathological significance. Gynecol Oncol. Jan. 2011;120(1):135-44.
Matthay et al., Acute lung injury and the acute respiratory distress syndrome: four decades of inquiry into pathogenesis and rational management. Am J Respir Cell Mol Biol. Oct. 2005;33(4):319-27.
Maury et al., Homozygosity for the Asn187 gelsolin mutation in Finnish-type familial amyloidosis is associated with severe renal disease. Genomics. Jul. 1992;13(3):902-3.
Pottiez et al., Mass spectrometric characterization of gelsolin isoforms. Rapid Commun Mass.Spectrom. Sep. 15, 2010;24(17):2620-4.
Robinson, Amyloid beta reverses MS-like disease in mice. Is it time to reevaluate amyloid elsewhere? Sep. 2012:16-17.
Simon et al., A matched crossover design for clinical trials. Contemp Clin Trials. Sep. 2007;28(5):638-46.
Vasconcellos et al., Coordinated inhibition of actin-induced platelet aggregation by plasma gelsolin and vitamin D-binding protein. Blood. Dec. 15, 1993;82(12):3648-57.
Kucan et al., Influence of topical steroids on bacterial proliferation in the burn wound. J Surg Res. Feb. 1978;24(2):79-82.
Rooney et al., Interleukin 1 beta in synovial fluid is related to local disease activity in rheumatoid arthritis. Rheumatol Int. 1990;10(5):217-9.
Martel, Bronchopneumonia: Causes, Symptoms & Diagnosis. Healthline. Medically reviewed by George Krucik, M.D. Published Jul. 12, 2012. www.healthline.com/health/bronchopneumonia#Overview1.
Yang et al., Plasma Gelsolin Improves Lung Host Defense against Pneumonia by Enhancing Macrophage NOS3 Function. Am J Physiol Lung Cell Mol Physiol. May 8, 2015. doi:10.1152/ajplung.00094.2015.
Kozlova et al., [Use of fragmin in program hemodialysis of patients with terminal chronic renal failure]. Klin Med (Mosk). 2005;83(9):45-9. Russian. PubMed PMID: 16279040. Abstract.
Vincent et al., Platelet function in sepsis. Crit Care Med. May 2002;30(5):S313-S317.
Cheng et al., Gelsolin Inhibits the Inflammatory Process Induced by LPS. Cell Physiol Biochem. 2017;41(1):205-212. doi: 10.1159/000456043. Epub Jan. 20, 2017.
Magnuson-Osborn et al., Human plasma Gelsolin inhibits cellular responses to platelet activating factor (PAF). Blood. 2005. 106:996a. Abstract Only. www.bloodjournal.org/content/106/11/3568?sso-checked=true. Accessed on Jan. 10, 2017.

(56) References Cited

OTHER PUBLICATIONS

U.S. Appl. No. 12/018,782, filed Jan. 23, 2008, Abandoned, 2008-0261260.
U.S. Appl. No. 12/026,761, filed Feb. 6, 2008, Abandoned, 2008-0125370.
U.S. Appl. No. 13/861,578, filed Oct. 7, 2009, Granted, now U.S. Pat. No. 8,440,622.
U.S. Appl. No. 13/861,578, filed Apr. 12, 2013, Published, 2013-0230455.
U.S. Appl. No. 12/225,128, filed Mar. 22, 2010, Granted, now U.S. Pat. No. 8,198,094.
U.S. Appl. No. 12/225,132, filed Apr. 25, 2012, Published, 2012-0208743.
U.S. Appl. No. 10/574,034, filed May 2, 2007, Published, 2007-0238655.
U.S. Appl. No. 11/391,540, filed Mar. 28, 2006, Published, 2007-0238668.
U.S. Appl. No. 12/358,868, filed Jan. 23, 2009, Published, 2009-0258330.
EP 10185573.2, dated May 16, 2012, Extended European Search Report.
EP 13186249.2, dated Feb. 17, 2014, Extended European Search Report.
U.S. Appl. No. 15/407,458, filed Jan. 17, 2017, Thadhani et al.

\* cited by examiner

USE OF GELSOLIN TO TREAT INFECTIONS

RELATED APPLICATIONS

This application claims priority under 35 U.S.C. § 119(e) from U.S. Provisional Application Ser. No. 60/570,233 with a filing date of May 12, 2004 and entitled "Inhibition of Lipolysaccharide (LPS) Endotoxin by Gelsolin and Gelsolin Analogs" incorporated herein in its entirety by reference.

FIELD OF THE INVENTION

The invention is directed to the use of gelsolin to treat infections and sepsis and to the use of gelsolin to monitor and evaluate treatments of infections. The invention also provides methods for up-regulating interleukin expression and methods for down-regulating pro-inflammatory cytokine expression.

BACKGROUND OF THE INVENTION

Despite significant advances in diagnosis and therapy, infections and sepsis remain a major cause of morbidity and mortality throughout the world. Even with aggressive management, many patients with severe infections develop complications and some die. Sepsis claims more than 200,000 lives in the United States annually (Angus, D. C. & Wax, R. S. (2001) *Crit Care Med* 29, S109-16). An intense inflammatory response accompanies the early phase of sepsis with markedly increased plasma levels of pro-inflammatory cytokines (Riedemann, N. C., Guo, R. F. & Ward, P. A. (2003) *Nat Med* 29, 517-24), in addition to other biochemical abnormalities. Much concerted research has gone into attempts at inhibition of specific inflammatory mediators in hope of developing pharmacologic treatments for sepsis. Nevertheless, activated protein C (APC) is the only drug proven to reduce the mortality of severe sepsis with an absolute reduction of death by 6% (Bernard, G. R., Vincent, J. L., Laterre, P. F., LaRosa, S. P., Dhainaut, J. F., Lopez-Rodriguez, A., Steingrub, J. S., Garber, G. E., Helterbrand, J. D., Ely, E. W. & Fisher, C. J., Jr. (2001) *N Engl J Med* 344, 699-709).

The negative health effects of infections and sepsis provide a strong incentive to identify new treatments as well as improved tests and approaches to evaluate therapy of infections and sepsis.

SUMMARY OF THE INVENTION

This invention is based on the surprising discovery that gelsolin treats infections and protects against the toxic manifestations of infections. We have found that mice injected with gelsolin subsequent to the exposure to an infectious agent unexpectedly survived better than mice given saline. Thus, the invention involves in one aspect, the administration of gelsolin to a subject to treat an infection. The invention is also directed to methods of using gelsolin to treat the biological effects of infections.

Gelsolin (GSN), specifically cytoplasmic gelsolin (cGSN), first discovered as an intracellular actin-binding protein involved in cell motility (Yin, H. L. & Stossel, T. P. (1979) *Nature* 281, 583-6) is also an abundant secretory protein (Yin, H. L., Kwiatkowski, D. J., Mole, J. E. & Cole, F. S. (1984) *J Biol Chem* 259, 5271-6). The exported isoform of gelsolin, designated plasma gelsolin (pGSN), has 25 additional amino acids and originates from alternative splicing of a single gene (Kwiatkowski, D. J., Stossel, T. P., Orkin, S. H., Mole, J. E., Colten, H. R. & Yin, H. L. (1986) *Nature* 323, 455-8).

In each of the following aspects and embodiments of the invention, the use of pGSN is preferred.

According to one aspect of the invention, methods of treating an infection in a subject are provided. The methods include administering gelsolin to the subject having or at risk of having an infection in an effective amount to treat the infection. The infection may be caused by a gram-positive bacterium, an acid-fast *bacillus*, a spirochete, an actinomycete, a virus, a fungus, a parasite, *Ureaplasma* species including *Ureaplasma urealyticum*, *Mycoplasma* species including *Mycoplasma pneumonia*, *Rickettsia* species, *Chlamydia* species including *Chlamydia psittaci*, *Chlamydia trachomatis* and *Chlamydia pneumoniae*, and *Pneumocystis* species including *Pneumocystis carinii*. In some embodiments, the subject is otherwise free of indications calling for treatment with gelsolin. In some embodiments, the gelsolin is administered subsequent to exposure of the subject to the infection. In certain embodiments, the gelsolin is administered at least about 1, 2, 3, 4, 5, 6, 7, 8, 9, 10, 11, 12, 13, 14, 15, 16, 17, 18, 19, 20, 21, 22, 23, or 24 hours subsequent to exposure of the subject to the infection. In some embodiments, the gelsolin is administered at least about 1, 2, 3, 4, 5, 6, 7, or more days subsequent to exposure of the subject to the infection.

According to yet another aspect of the invention, methods of treating a gram-negative bacterial infection in a subject are provided. The methods include administering gelsolin to the subject in an effective amount at a time subsequent to the exposure of the subject to a gram-negative bacterial infection. In some embodiments, the subject is otherwise free of indications calling for treatment with gelsolin. In some embodiments, the gelsolin is administered at least about one hour subsequent to exposure of the subject to the gram-negative bacterial infection. In certain embodiments, the gelsolin is administered at least about 2, 3, 4, 5, 6, 7, 8, 9, 10, 11, 12, 13, 14, 15, 16, 17, 18, 19, 20, 21, 22, 23, or 24 hours subsequent to after exposure of the subject to the gram-negative bacterial infection. In some embodiments, the gelsolin is administered at least about 1, 2, 3, 4, 5, 6, 7, or more days subsequent to exposure of the subject to the gram-negative bacterial infection. In some embodiments, gelsolin is administered prior to exposure of the subject to the gram-negative bacterial infection.

According to another aspect of the invention, methods of treating or preventing the effects of lipopolysaccharide endotoxin (LPS) in a subject are provided. The methods include administering to the subject an effective amount of gelsolin at a time subsequent to LPS exposure to protect the subject against the effects of LPS. In some embodiments, the subject is otherwise free of indications calling for treatment with gelsolin. In some embodiments, the gelsolin is administered at least about one hour subsequent to the exposure of the subject to the LPS. In certain embodiments, the gelsolin is administered at least about 2, 3, 4, 5, 6, 7, 8, 9, 10, 11, 12, 13, 14, 15, 16, 17, 18, 19, 20, 21, 22, 23, or 24 or more hours subsequent to exposure of the subject to LPS. In some embodiments, the gelsolin is administered at least about 1, 2, 3, 4, 5, 6, 7, or more days subsequent to exposure of the subject to LPS.

According to another aspect of the invention, methods of treating or preventing gram-negative bacterial septic shock in a subject exposed to LPS are provided. The methods include administering to the subject an effective amount of gelsolin at a time subsequent to LPS exposure to treat the gram-negative bacterial septic shock in the subject. In some embodiments, the subject is free of indications calling for treatment with gelsolin. In some embodiments, the gelsolin is administered at least about one hour subsequent to exposure of the subject to LPS. In certain embodiments, the gelsolin is administered at least about 2, 3, 4, 5, 6, 7, 8, 9, 10, 11, 12, 13, 14, 15, 16, 17, 18, 19, 20, 21, 22, 23, or 24 hours subsequent to exposure of the subject to LPS. In some embodiments, the gelsolin is administered at least about 1, 2, 3, 4, 5, 6, 7, or more days subsequent to exposure of the subject to LPS.

According to another aspect of the invention, a method for up-regulating interleukin (IL) expression in a subject is provided. The method involves administering gelsolin to the subject in an effective amount to up-regulate IL expression in the subject. In some embodiments, the subject is free of indications calling for treatment with gelsolin. Up-regulation of IL expression may be either due to increased expression of the IL or due to decreased degradation of the IL or a combination of an increased expression of the IL and a decreased degradation of the IL.

In some embodiments, the expression of IL is increased by at least approximately 25% relative to control. In other embodiments, the expression of IL is increased by at least approximately 50% or 75% relative to control. In some embodiments, the expression of IL is increased by at least approximately 2-fold relative to control. In some embodiments, the IL expression is increased at least approximately 3-fold, 5-fold, 10-fold, 50-fold, 100-fold, 200-fold, 500-fold, or 1000-fold relative to control. In general, the IL expression level in a control is the level of IL expression in a subject to whom gelsolin was not administered but is otherwise identical to the treated subject. Methods of measuring IL levels are known to those of ordinary skill in the art.

According to another aspect of the invention, a method for up-regulating IL expression in vitro is provided. The method involves contacting a cell capable of expressing IL with a sufficient amount of gelsolin to up-regulate the level of IL expression in the cell. In some embodiments, the expression of IL is increased by at least approximately 25% relative to control. In other embodiments, the expression of IL is increased by at least approximately 50% or 75% relative to control. In some embodiments, the expression of IL is increased by at least approximately 2-fold relative to control. In general, the level of IL expression in a control is that level of expression in a cell that is not contacted with gelsolin but is otherwise identically treated to the cell contacted with gelsolin. In some embodiments, the IL expression is increased at least approximately 3-fold, 5-fold, 10-fold, 50-fold, 100-fold, 200-fold, 500-fold, or 1000-fold relative to control. Methods of measuring IL levels are known to those of ordinary skill in the art.

The time period in which the IL expression is increased is, at least in part, a function of the cell type and on the specific culture vessel used. In general, this time period ranges from 2-3 hours (for short-term increase) to about 2-3 days (for medium-term increase) to several weeks (for long-term increase). Routine procedures known to those of ordinary skill in the art can be used to determine the level of IL expression as a function increasing doses of gelsolin or increasing incubation time or of the cells with gelsolin. One preferred IL is IL-10.

According to another aspect of the invention, a method for down-regulating pro-inflammatory cytokine expression in a subject is provided. The method involves administering to the subject gelsolin in an effective amount to down-regulate pro-inflammatory cytokine expression in the subject. In some embodiments, the subject is otherwise free of indications calling for treatment with gelsolin. Down-regulation of pro-inflammatory cytokine expression may be either due to a decreased expression of the cytokine or due to an increased degradation of the cytokine or a combination of a decreased expression of the cytokine and an increased degradation of the cytokine. In general, the expression of pro-inflammatory cytokine is decreased by at least approximately 10% relative to control. In some embodiments, the expression of pro-inflammatory cytokine is decreased by at least approximately 20%, 30%, 40%, 50%, 60%, 70%, 80%, 90%, 95%, or 99% relative to control. In some embodiments the expression of pro-inflammatory cytokine is decreased by 100% relative to control. In general, the pro-inflammatory cytokine expression level in a control is the level of pro-inflammatory cytokine expression in a subject to whom gelsolin was not administered but is otherwise identical to the treated subject. Methods of measuring pro-inflammatory cytokine levels are known to those of ordinary skill in the art. One preferred pro-inflammatory cytokine is IL-1β. Another preferred pro-inflammatory cytokine is IFN-α.

According to one aspect of the invention, a method for down-regulating expression of pro-inflammatory cytokines in vitro is provided. The method involves contacting a cell capable of expressing a pro-inflammatory cytokine with a sufficient amount of gelsolin to down-regulate the level of pro-inflammatory cytokine expression in the cell. In general, the expression of a pro-inflammatory cytokine is decreased by at least approximately 10% relative to control. In general, the level of a pro-inflammatory cytokine expression in a control is that level of expression in a cell that is not contacted with gelsolin but is otherwise identically treated to the cell contacted with gelsolin. In some embodiments, the pro-inflammatory cytokine expression is decreased at least approximately 20%, 30%, 40%, 50%, 60%, 70%, 80%, 90%, 95%, or 99% relative to control. In some embodiments the expression of pro-inflammatory cytokine is decreased by 100% relative to control. Methods of measuring pro-inflammatory cytokine levels are known to those of ordinary skill in the art.

The time period in which the pro-inflammatory cytokine expression is decreased is, at least in part, a function of the cell type and on the specific culture vessel used. In general, this time period ranges from 2-3 hours (for short-term decrease) to about 2-3 days (for medium-term decrease) to several weeks (for long-term decrease). Routine procedures known to those of ordinary skill in the art can be used to determine the level of pro-inflammatory cytokine expression as a function of increasing doses of gelsolin or increasing incubation time of the cells with the gelsolin.

According to another aspect of the invention, a method for treating a subject to reduce the risk of an infection is provided. The method comprises selecting a subject on the basis that the subject is known to have a below-normal level of gelsolin and administering to the subject an agent for reducing the risk of an infection in an amount effective to lower the subject's risk of developing an infection. The agent may be gelsolin and/or an anti-infective agent. In some embodiments, the subject is otherwise free of indications calling for treatment with gelsolin.

A "below-normal level of gelsolin" is a gelsolin level is at least 10% less than the measured mean level for a given population of subjects. The mean gelsolin level can depend upon the particular population of subjects. For example, an apparently healthy population will have a different "normal" range of gelsolin than will a population of subjects which have had a prior infection or other condition. In some embodiments, the gelsolin level is at least 10% less than the measured mean level for a given population of subjects. In other embodiments, the gelsolin level is at least 20% less than the measured mean level for a given population of subjects. In still other embodiments, the gelsolin level is at least 30%, 40%, 50%, 60%, 70%, 80%, 90%, 95%, 99% or 100% less than the measured mean level for a given population of subjects. In one of the preferred embodiments, the gelsolin level is below about 2.4 µM/L (micromoles/Liter) of plasma.

In some embodiments the subject is otherwise free of indications calling for treatment with the agent. When the agent is an anti-infective agent, a subject free of indications calling for treatment with an anti-infective agent is a subject who has no signs or symptoms of an infection. Signs and symptoms of an infection are well known to those of ordinary skill in the art. Gelsolin is indicated for the treatment of actin-related disorders such as Adult Respiratory Distress Syndrome (ARDS), fulminant hepatic necrosis, acute renal failure, muscle injury, disorders characterized by elevated levels of BUN and/or creatinine. Actin-related disorders are known to those of ordinary skill in the art.

In other embodiments, the subject is apparently healthy. As used herein an "apparently healthy subject" is a subject who has no signs and/or symptoms of a disease.

The infection may be caused by one or more of a number of organisms such as a bacterium, a virus, a fungus, or a parasite.

The anti-infective agent may be an anti-bacterial, an anti-viral, and anti-fungal, or an anti-parasitic agent.

Examples of anti-bacterial agents, anti-viral agents, anti-fungal agents, and anti-parasitic agents are listed below.

The gelsolin may be administered orally, sublingually, buccally, intranasally, intravenously, intramuscularly, intrathecally, intraperitoneally, subcutaneously, intradermally, topically, rectally, vaginally, intrasynovially, or intravitreously.

According to another aspect of the invention, a method for evaluating the efficacy of a therapy with a therapeutic agent other than a gelsolin for treating or preventing an infection is provided. The method involves obtaining a level of a gelsolin in a subject undergoing the therapy to treat or prevent an infection. The level of the gelsolin is compared to a predetermined value corresponding to a control level of gelsolin (e.g., in an apparently healthy population). A determination of whether the level of the gelsolin is below the predetermined level is indicative of whether the therapy is efficacious. In some embodiments, obtaining a level of the gelsolin is repeated so as to monitor the human subject's level of the gelsolin over time.

According to yet another aspect of the invention method for deciding on the course of a therapy in a subject is provided. The method involves obtaining a level of gelsolin in a subject undergoing a therapy to treat an infection. The level of gelsolin is compared to a predetermined value corresponding to a control level of gelsolin (e.g., in an apparently healthy population). Whether the level of gelsolin obtained is above or below the predetermined level is determined and the course of the therapy is decided based on such determination. In some embodiments, obtaining a level of gelsolin is repeated so as to monitor the subject's level of gelsolin over time.

According to yet another aspect of the invention, a method for treating a subject with a decreased level of gelsolin is provided. The method involves treating the subject with a first therapy for treating an infection. A level of gelsolin in the subject is obtained. The level of gelsolin is compared to a predetermined value corresponding to a control level of gelsolin (e.g., in an apparently healthy population). If the predetermined level of gelsolin is not reached, the subject is treated with a second therapy for treating an infection and the level of the gelsolin is measured and compared to the predetermined level of the gelsolin until the predetermined level of the gelsolin is reached.

According to still yet another aspect of the invention, a method for characterizing an subject's risk profile of developing a future infection is provided. The method comprises obtaining a level of gelsolin in the subject and comparing the level of the marker to a predetermined value. The subject's risk profile of developing an infection is characterized based upon the level of gelsolin in comparison to the predetermined value. A level of gelsolin below the predetermined level is indicative that the subject is at an elevated risk of developing an infection and a level of gelsolin above the predetermined level is indicative that the subject is not at an elevated risk of developing an infection.

In some embodiments, the predetermined value is about 2.4 µM/L of plasma or lower.

In some embodiments, the subject is an apparently healthy subject.

Each of the limitations of the invention can encompass various embodiments of the invention. It is, therefore, anticipated that each of the limitations of the invention involving any one element or combinations of elements can be included in each aspect of the invention. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

These and other aspects of the invention will be described in more detail below in connection with the detailed description of the invention.

All documents identified in this application are incorporated in their entirety herein by reference.

BRIEF DESCRIPTION OF DRAWINGS

The figures are illustrative only and are not required for enablement of the invention disclosed herein.

DETAILED DESCRIPTION OF THE INVENTION

Figure 1A:
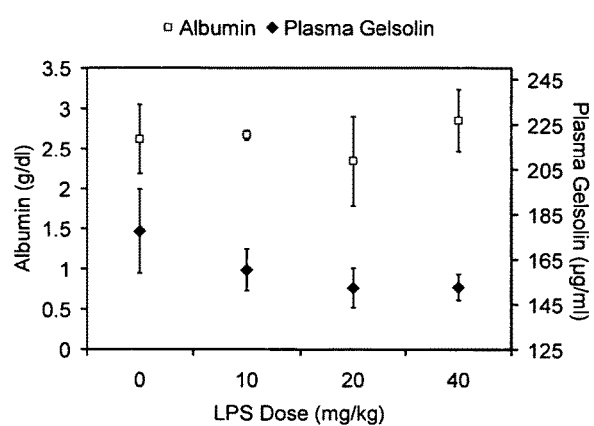
FIG. 1 is a graph of plasma gelsolin levels in septic mice. (A) Mice were injected with increasing doses of non-lethal LPS intraperitoneally (IP) and then bled 24 hours later. pGSN level inversely correlated with LPS doses ($P<0.05$, Spearman Correlation). Conversely, albumin was unchanged. (B) Mice were subjected to CLP (Cecal Ligation and Puncture) or no surgery and plasma collected 24 hours later. The left graph shows that pGSN levels of mice subjected to CLP were significantly lower than control mice ($P<0.001$) while the right graph shows plasma albumin levels were actually higher in CLP mice ($P=0.02$).
Figure 1B:
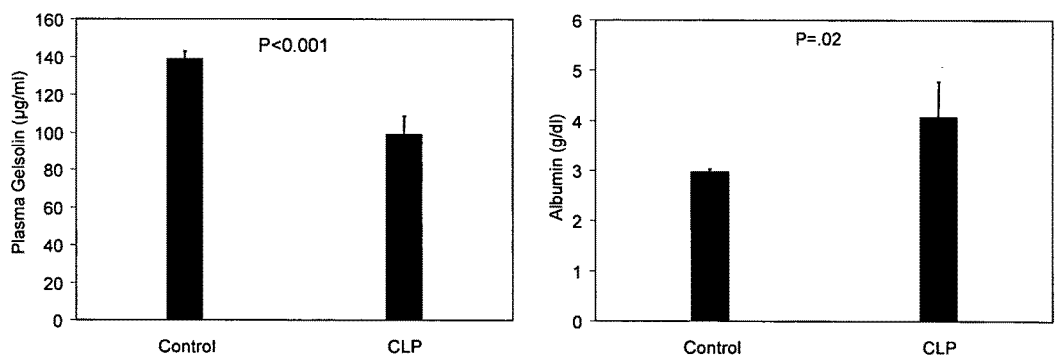

The present invention is based, in part, on the discovery that the administration of gelsolin protects a subject from infection. Thus, the invention includes, in some aspects, administering gelsolin to a subject for the treatment of infection in the subject. We have discovered that gelsolin antagonizes the toxic effects lipopolysaccharide endotoxin (LPS), the cell wall material of gram-negative bacteria known to be responsible for many of the manifestations of the gram-negative bacterial infection.

We have also discovered that the administration of gelsolin to a subject following exposure of the subject to an infection can treat an infection and can reduce or prevent the toxic effects of the infection in the subject. Preferably, the treatment of an infection involves treatment of the signs and symptoms of the infection.

The term "treatment" or "treating" is intended to include prophylaxis, amelioration, prevention or cure of infections.

As used herein the term "subject" means any mammal that may be in need of treatment. Subjects include but are not limited to: humans, non-human primates, cats, dogs, sheep, pigs, horses, cows, rodents such as mice, hamsters, and rats. Preferred subjects are human subjects.

As used herein the term "gelsolin" encompasses wild type gelsolin (GenBank accession No.: X04412), isoforms, analogs, variants, fragments or functional derivatives of gelsolin. Gelsolin encompasses native as well as synthetic and recombinant gelsolin and gelsolin analogs. Gelsolin, specifically cGSN, is an abundant secretory protein (Yin, H. L., Kwiatkowski, D. J., Mole, J. E. & Cole, F. S. (1984) *J Biol Chem* 259, 5271-6). The exported isoform of gelsolin, pGSN, has 25 additional amino acids and originates from alternative splicing of a single gene (Kwiatkowski, D. J., Stossel, T. P., Orkin, S. H., Mole, J. E., Colten, H. R. & Yin, H. L. (1986) *Nature* 323, 455-8). In the different aspects and embodiments of the invention, the use of pGSN is preferred.

A "gelsolin analog" refers to a compound substantially similar in function to either the native gelsolin or to a fragment thereof. Gelsolin analogs include biologically active amino acid sequences substantially similar to the gelsolin sequences and may have substituted, deleted, elongated, replaced, or otherwise modified sequences that possess bioactivity substantially similar to that of gelsolin. For example, an analog of gelsolin is one which does not have the same amino acid sequence as gelsolin but which is sufficiently homologous to gelsolin so as to retain the bioactivity of gelsolin. Bioactivity can be determined, for example, by determining the properties of the gelsolin analog and/or by determining the ability of the gelsolin analog to reduce or prevent the effects of an infection. One example of gelsolin bioactivity assay is gelsolin's ability to stimulate actin nucleation. Gelsolin bioactivity assays are described in the Example and are known to those of ordinary skill in the art.

A "fragment" is meant to include any portion of a gelsolin molecule which provides a segment of gelsolin which maintains the bioactivity of gelsolin; the term is meant to include gelsolin fragments which are made from any source, such as, for example, from naturally-occurring peptide sequences, synthetic or chemically-synthesized peptide sequences, and genetically engineered peptide sequences.

A "variant" of gelsolin is meant to refer to a compound substantially similar in structure and bioactivity either to native gelsolin, or to a fragment thereof.

A "functional derivative" of gelsolin is a derivative which possesses a bioactivity that is substantially similar to the bioactivity of gelsolin. By "substantially similar" is meant activity which is quantitatively different but qualitatively the same. For example, a functional derivative of gelsolin could contain the same amino acid backbone as gelsolin but also contains other modifications such as post-translational modifications such as, for example, bound phospholipids, or covalently linked carbohydrate, depending on the necessity of such modifications for the performance of the diagnostic assay or therapeutic treatment. As used herein, the term is also meant to include a chemical derivative of gelsolin. Such derivatives may improve gelsolin's solubility, absorption, biological half life, etc. The derivatives may also decrease the toxicity of gelsolin, or eliminate or attenuate any undesirable side effect of gelsolin, etc. Derivatives and specifically, chemical moieties capable of mediating such effects are disclosed in Remington's Pharmaceutical Sciences (1980). Procedures for coupling such moieties to a molecule such as gelsolin are well known in the art. The term "functional derivative" is intended to include the "fragments," "variants," "analogues," or "chemical derivatives" of gelsolin.

The invention involves in some aspects, methods for treating infection in a subject. The methods involve administering gelsolin to a subject for treating the infection. The subject is known to have, is suspected of having been exposed, or is at risk of being exposed, or who has been exposed to an infection. The gelsolin is administered in an amount effective to treat the infection in the subject.

A response to a treatment method of the invention can, for example, be measured by determining the physiological effects of the treatment, such as the decrease or lack of symptoms following administration of the treatment.

An "infection" or "infectious disease", as used herein, refers to a disorder arising from the invasion of a host, superficially, locally, or systemically, by an infectious organism. Infectious organisms include bacteria, viruses, parasites, fungi, and protozoa.

Bacteria include gram-negative and gram-positive bacteria. Examples of gram-positive bacteria include *Pasteurella* species, *Staphylococcus* species including *Staphylococcus aureus*, *Streptococcus* species including *Streptococcus pyogenes* group A, *Streptococcus* viridans group, *Streptococcus agalactiae* group B, *Streptococcus bovis*, *Streptococcus* anaerobic species, *Streptococcus pneumoniae*, and *Streptococcus faecalis*, *Bacillus* species including *Bacillus anthracis*, *Corynebacterium* species including *Corynebacterium diphtheriae*, aerobic *Corynebacterium* species, and anaerobic *Corynebacterium* species, *Diphtheroids* species, *Listeria* species including *Listeria monocytogenes*, *Erysipelothrix* species including *Erysipelothrix rhusiopathiae*, *Clostridium* species including *Clostridium perfringens*, *Clostridium tetani*, and *Clostridium difficile*.

Gram-negative bacteria include *Neisseria* species including *Neisseria gonorrhoeae* and *Neisseria meningitidis*, *Branhamella* species including *Branhamella catarrhalis*, *Escherichia* species including *Escherichia coli*, *Enterobacter* species, *Proteus* species including *Proteus mirabilis*, *Pseudomonas* species including *Pseudomonas aeruginosa*, *Pseudomonas mallei*, and *Pseudomonas pseudomallei*, *Klebsiella* species including *Klebsiella pneumoniae*, *Salmonella* species, *Shigella* species, *Serratia* species, *Acinetobacter* species; *Haemophilus* species including *Haemophilus influenzae* and *Haemophilus ducreyi*, *Brucella* species, *Yersinia* species including *Yersinia pestis* and *Yersinia enterocolitica*, *Francisella* species including *Francisella tularensis*, *Pasturella* species including *Pasteurella multocida*, *Vibrio cholerae*, *Flavobacterium* species, *meningosepticum*, *Campylobacter* species including *Campylobacter jejuni*, *Bacteroides* species (oral, pharyngeal) including *Bacteroides fragilis*, *Fusobacterium* species including *Fusobacterium nucleatum*, *Calymmatobacterium granulomatis*, *Streptobacillus* species including *Streptobacillus moniliformis*, *Legionella* species including *Legionella pneumophila*.

Other types of bacteria include acid-fast bacilli, spirochetes, and actinomycetes.

Examples of acid-fast bacilli include *Mycobacterium* species including *Mycobacterium tuberculosis* and *Mycobacterium leprae*.

Examples of spirochetes include *Treponema* species including *Treponema pallidum*, *Treponema pertenue*, *Borrelia* species including *Borrelia burgdorferi* (Lyme disease), and *Borrelia recurrentis*, and *Leptospira* species.

Examples of actinomycetes include: *Actinomyces* species including *Actinomyces israelii*, and *Nocardia* species including *Nocardia asteroides*.

Examples of viruses include but are not limited to: Retroviruses, human immunodeficiency viruses including HIV-1, HDTV-III, LAVE, HTLV-III/LAV, HIV-III, HIV-LP, Cytomegaloviruses (CMV), Picornaviruses, polio viruses, hepatitis A virus, enteroviruses, human Coxsackie viruses, rhinoviruses, echoviruses, Calciviruses, Togaviruses, equine encephalitis viruses, rubella viruses, Flaviruses, dengue viruses, encephalitis viruses, yellow fever viruses, Coronaviruses, Rhabdoviruses, vesicular stomatitis viruses, rabies viruses, Filoviruses, ebola virus, Paramyxoviruses, parainfluenza viruses, mumps virus, measles virus, respiratory syncytial virus (RSV), Orthomyxoviruses, influenza viruses, Bungaviruses, Hantaan viruses, phleboviruses and Nairo viruses, Arena viruses, hemorrhagic fever viruses, reoviruses, orbiviruses, rotaviruses, Birnaviruses, Hepadnaviruses, Hepatitis B virus, parvoviruses, Papovaviridae, papilloma viruses, polyoma viruses, Adenoviruses, Herpesviruses including herpes simplex virus 1 and 2, varicella zoster virus, Poxviruses, variola viruses, vaccinia viruses, Irido viruses, African swine fever virus, delta hepatitis virus, non-A, non-B hepatitis virus, Hepatitis C, Norwalk viruses, astroviruses, and unclassified viruses.

Examples of fungi include, but are not limited to: *Cryptococcus* species including *Crytococcus neoformans*, *Histoplasma* species including *Histoplasma capsulatum*, *Coccidioides* species including *Coccidiodes immitis*, *Paracoccidioides* species including *Paracoccidioides brasiliensis*, *Blastomyces* species including *Blastomyces dermatitidis*, *Chlamydia* species including *Chlamydia trachomatis*, *Candida* species including *Candida albicans*, *Sporothrix* species including *Sporothrix schenckii*, *Aspergillus* species, and fungi of mucormycosis.

Other infectious organisms include parasites. Parasites include *Plasmodium* species, such as *Plasmodium* species including *Plasmodium falciparum*, *Plasmodium malariae*, *Plasmodium ovale*, and *Plasmodium vivax* and *Toxoplasma gondii*. Blood-borne and/or tissues parasites include *Plasmodium* species, *Babesia* species including *babesia microti* and *Babesia divergens*, *Leishmania* species including *Leishmania tropica*, *Leishmania* species, *Leishmania braziliensis*, *Leishmania donovani*, *Trypanosoma* species including *Trypanosoma gambiense*, *Trypanosoma rhodesiense* (African sleeping sickness), and *Trypanosoma cruzi* (Chagas' disease).

Other medically relevant microorganisms have been described extensively in the literature, e.g., see C. G. A Thomas, *Medical Microbiology*, Bailliere Tindall, Great Britain 1983, the entire contents of which is hereby incorporated by reference.

In another aspect of the invention, a method for up-regulating interleukin (IL) expression in a subject is provided. The method comprises administering to the subject gelsolin in an effective amount to up-regulate IL expression. Up-regulation of IL may be measured by determining the physiological effects of the IL following administration of gelsolin. Physiological effects of IL are known to those of ordinary skill in the art.

In another aspect of the invention, a method for down-regulating a pro-inflammatory cytokine expression in a subject is provided. The method comprises administering gelsolin to the subject in an effective amount to down-regulate pro-inflammatory cytokine expression. Down-regulation of pro-inflammatory cytokines may be measured by determining the physiological effects of pro-inflammatory cytokines following administration of gelsolin. Physiological effects of pro-inflammatory cytokines are known to those of ordinary skill in the art.

Other assays are known to one of ordinary skill in the art and can be employed for measuring the level of the response.

In another aspect of the invention, a method for monitoring a subject is provided. The method involves obtaining a level of gelsolin in a subject undergoing therapy to treat an infection. The level of gelsolin is compared to a predetermined value corresponding to a control level of gelsolin (e.g., in an apparently healthy population). A determination of whether the level of gelsolin is below a predetermined level is indicative of whether the subject would benefit from continued therapy with the same therapy or would benefit from a change in therapy. In some embodiments, obtaining a level of gelsolin is repeated so as to monitor the subject's levels of gelsolin over time. In some embodiments, the subject may have been undergoing the therapy for at least 1, 2, 3, 4, 5, 6, 7 or more days. In some embodiments, the subject may have been undergoing the therapy for at least 1, 2, 3, 4 or more weeks.

A change in therapy with gelsolin refers to an increase in the dose of the gelsolin, a switch from gelsolin to another agent, the addition of another agent to the gelsolin therapeutic regimen, or a combination thereof.

According to another aspect of the invention, a method for evaluating the efficacy of a therapy for treating or reducing the risk of an infection is provided. The method involves obtaining a level of gelsolin in a subject undergoing therapy to treat or prevent an infection. The level of gelsolin is compared to a predetermined value corresponding to a control level of gelsolin (e.g., in an apparently healthy population). A determination of whether the level of gelsolin is below a predetermined level is indicative of whether the therapy is efficacious. In some embodiments, the subject may have been undergoing the therapy for at least 1, 2, 3, 4, 5, 6, 7 or more days. In some embodiments, the human subject may have been undergoing the therapy for at least 1, 2, 3, 4 or more weeks.

One aspect of the invention is directed to the measurement of gelsolin to guide treatments in order to improve outcome in subjects. On-therapy levels of gelsolin have predictive value for response to treatments of infections or sepsis. The on-therapy levels of gelsolin are additive to prior art predictors of outcome in infections.

Subjects who would benefit from this aspect of this invention are subjects who are undergoing therapy to treat or prevent an infection (i.e., a subject "on-therapy"). A subject on-therapy is a subject who already has been diagnosed and is in the course of treatment with a therapy for treating an infection. The therapy can be any of the therapeutic agents referred to herein. The therapy also can be non-drug treatments. In important embodiments, the therapy is one which increases levels of gelsolin. In a particularly important embodiment, the therapy is a therapy with gelsolin. Preferred subjects are human subjects. The subject most likely to benefit from this invention is a human subject on-therapy and who has a gelsolin level below about 2.4 μM/L of plasma.

In some embodiments, the subject already has or had an infection. A subject who has or has had a primary (first) bacterial, viral, fungal, parasitic, or protozoal infection may be at an elevated risk of a secondary (second) infection. In some embodiments, the subject has not had a primary infection, but is at an elevated risk of having an infection because the subject has one or more risk factors to have an infection. Risk factors for a primary infection include: immunosuppression, immunocompromise, age, trauma, burns (e.g., thermal burns), surgery, foreign bodies, cancer, newborns especially newborns born prematurely. The degree of risk of an infection depends on the multitude and the severity or the magnitude of the risk factors that the subject has. Risk charts and prediction algorithms are available for assessing the risk of an infection in a subject based on the presence and severity of risk factors.

Other methods of assessing the risk of an infection in a subject are known by those of ordinary skill in the art In still other embodiments, the subject has had a primary infection and has one or more other risk factors.

The preferred treatment of the instant invention is gelsolin. Gelsolin may be administered alone, in a pharmaceutical composition or combined with other therapeutic regimens. Gelsolin and other therapeutic agent(s) may be administered simultaneously or sequentially. When the other therapeutic agents are administered simultaneously they can be administered in the same or separate formulations, but are administered at the same time. The other therapeutic agents may be administered sequentially with one another and with gelsolin when the administration of the other therapeutic agents and the gelsolin is temporally separated. The separation in time between the administration of these compounds may be a matter of minutes or it may be longer. Other therapeutic agents include but are not limited to anti-infective agent(s). Examples of anti-infective agent(s) include: anti-bacterial agent(s), anti-viral agent(s), anti-fungal agent(s) or anti-protozoal agent(s).

Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit the growth or function of bacteria. Anti-bacterial agents include antibiotics as well as other synthetic or natural compounds having similar functions. Antibiotics, typically, are low molecular weight molecules which are produced as secondary metabolites by cells, such as microorganisms. In general, antibiotics interfere with one or more bacterial functions or structures which are specific for the microorganism and which are not present in host cells.

A large class of anti-bacterial agents is antibiotics. Antibiotics that are effective for killing or inhibiting a wide range of bacteria are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Anti-bacterial agents are sometimes classified based on their primary mode of action. In general, anti-bacterial agents are cell wall synthesis inhibitors, cell membrane inhibitors, protein synthesis inhibitors, nucleic acid synthesis or functional inhibitors, and competitive inhibitors.

Anti-bacterial agents include but are not limited to aminoglycosides, β-lactam agents, cephalosporins, macrolides, penicillins, quinolones, sulfonamides, and tetracyclines. Examples of anti-bacterial agents include but are not limited to: Acedapsone, Acetosulfone Sodium, Alamecin, Alexidine, Amdinocillin Clavulanate Potassium, Amdinocillin, Amdinocillin Pivoxil, Amicycline, Amifloxacin, Amifloxacin Mesylate, Amikacin, Amikacin Sulfate, Aminosalicylic acid, Aminosalicylate sodium, Amoxicillin, Amphomycin, Ampicillin, Ampicillin Sodium, Apalcillin Sodium, Apramycin, Aspartocin, Astromicin Sulfate, Avilamycin, Avoparcin, Azithromycin, Azlocillin, Azlocillin Sodium, Bacampicillin Hydrochloride, Bacitracin, Bacitracin Methylene Disalicylate, Bacitracin Zinc, Bambermycins, Benzoylpas Calcium, Berythromycin, Betamicin Sulfate, Biapenem, Biniramycin, Biphenamine Hydrochloride, Bispyrithione Magsulfex, Butikacin, Butirosin Sulfate, Capreomycin Sulfate, Carbadox, Carbenicillin Disodium, Carbenicillin Indanyl Sodium, Carbenicillin Phenyl Sodium, Carbenicillin Potassium, Carumonam Sodium, Cefaclor, Cefadroxil, Cefamandole, Cefamandole Nafate, Cefamandole Sodium, Cefaparole, Cefatrizine, Cefazaflur Sodium, Cefazolin, Cefazolin Sodium, Cefbuperazone, Cefdinir, Cefditoren Pivoxil, Cefepime, Cefepime Hydrochloride, Cefetecol, Cefixime, Cefmenoxime Hydrochloride, Cefinetazole, Cefinetazole Sodium, Cefonicid Monosodium, Cefonicid Sodium, Cefoperazone Sodium, Ceforanide, Cefotaxime, Cefotaxime Sodium, Cefotetan, Cefotetan Disodium, Cefotiam Hydrochloride, Cefoxitin, Cefoxitin Sodium, Cefpimizole, Cefpimizole Sodium, Cefpiramide, Cefpiramide Sodium, Cefpirome Sulfate, Cefpodoxime Proxetil, Cefprozil, Cefroxadine, Cefsulodin Sodium, Ceftazidime, Ceftazidime Sodium, Ceftibuten, Ceftizoxime Sodium, Ceftriaxone Sodium, Cefuroxime, Cefuroxime Axetil, Cefuroxime Pivoxetil, Cefuroxime Sodium, Cephacetrile Sodium, Cephalexin, Cephalexin Hydrochloride, Cephaloglycin, Cephaloridine, Cephalothin Sodium, Cephapirin Sodium, Cephradine, Cetocycline Hydrochloride, Cetophenicol, Chloramphenicol, Chloramphenicol Palmitate, Chloramphenicol Pantothenate Complex, Chloramphenicol Sodium Succinate, Chlorhexidine Phosphanilate, Chloroxylenol, Chlortetracycline Bisulfate, Chlortetracycline Hydrochloride, Cilastatin, Cinoxacin, Ciprofloxacin, Ciprofloxacin Hydrochloride, Cirolemycin, Clarithromycin, Clavulanate Potassium, Clinafloxacin Hydrochloride, Clindamycin, Clindamycin Dextrose, Clindamycin Hydrochloride, Clindamycin Palmitate Hydrochloride, Clindamycin Phosphate, Clofazimine, Cloxacillin Benzathine, Cloxacillin Sodium, Cloxyquin, Colistimethate, Colistimethate Sodium, Colistin Sulfate, Coumermycin, Coumermycin Sodium, Cyclacillin, Cycloserine, Dalfopristin, Dapsone, Daptomycin, Demeclocycline, Demeclocycline Hydrochloride, Demecycline, Denofungin, Diaveridine, Dicloxacillin, Dicloxacillin Sodium, Dihydrostreptomycin Sulfate, Dipyrithione, Dirithromycin, Doxycycline, Doxycycline Calcium, Doxycycline Fosfatex, Doxycycline Hyclate, Doxycycline Monohydrate, Droxacin Sodium, Enoxacin, Epicillin, Epitetracycline Hydrochloride, Ertapenem, Erythromycin, Erythromycin Acistrate, Erythromycin Estolate, Erythromycin Ethylsuccinate, Erythromycin Gluceptate, Erythromycin Lactobionate, Erythromycin Propionate, Erythromycin Stearate, Ethambutol Hydrochloride, Ethionamide, Fleroxacin, Floxacillin, Fludalanine, Flumequine, Fosfomycin, Fosfomycin Tromethamine, Fumoxicillin, Furazolium Chloride, Furazolium Tartrate, Fusidate Sodium, Fusidic Acid, Gatifloxacin, Genifloxacin, Gentamicin Sulfate, Gloximonam, Gramicidin, Haloprogin, Hetacillin, Hetacillin Potassium, Hexedine, Ibafloxacin, Imipenem, Isoconazole, Isepamicin, Isoniazid, Josamycin, Kanamycin Sulfate, Kitasamycin, Levofloxacin, Levofuraltadone, Levopropylcillin Potassium, Lexithromycin, Lincomycin, Lincomycin Hydrochloride, Linezolid, Lomefloxacin, Lomefloxacin Hydrochloride, Lomefloxacin Mesylate, Loracarbef, Mafenide, Meclocycline, Meclocycline Sulfosalicylate, Megalomicin Potassium Phosphate, Mequidox, Meropenem, Methacycline, Methacycline Hydrochloride, Methenamine, Methenamine Hippurate, Methenamine Mandelate, Methicillin Sodium, Metioprim, Metronidazole Hydrochloride, Metronidazole Phosphate, Mezlocillin, Mezlocillin Sodium, Minocycline, Minocycline Hydrochloride, Mirincamycin Hydrochloride, Monensin, Monensin Sodium, Moxifloxacin Hydrochloride, Nafcillin Sodium, Nalidixate Sodium, Nalidixic Acid, Natamycin, Nebramycin, Neomycin Palmitate, Neomycin Sulfate, Neomycin Undecylenate, Netilmicin Sulfate, Neutramycin, Nifuradene, Nifuraldezone, Nifuratel, Nifuratrone, Nifurdazil, Nifurimide, Nifurpirinol, Nifurquinazol, Nifurthiazole, Nitrocycline, Nitrofurantoin, Nitromide, Norfloxacin, Novobiocin Sodium, Ofloxacin, Ormetoprim, Oxacillin Sodium, Oximonam, Oximonam Sodium, Oxolinic Acid, Oxytetracycline, Oxytetracycline Calcium, Oxytetracycline Hydrochloride, Paldimycin, Parachlorophenol, Paulomycin, Pefloxacin, Pefloxacin Mesylate, Penamecillin, Penicillin G Benzathine, Penicillin G Potassium, Penicillin G Procaine, Penicillin G Sodium, Penicillin V, Penicillin V Benzathine, Penicillin V Hydrabamine, Penicillin V Potassium, Pentizidone Sodium, Phenyl Aminosalicylate, Piperacillin, Piperacillin Sodium, Pirbenicillin Sodium, Piridicillin Sodium, Pirlimycin Hydrochloride, Pivampicillin Hydrochloride, Pivampicillin Pamoate, Pivampicillin Probenate, Polymyxin B Sulfate, Porfiromycin, Propikacin, Pyrazinamide, Pyrithione Zinc, Quindecamine Acetate, Quinupristin, Racephenicol, Ramoplanin, Ranimycin, Relomycin, Repromicin, Rifabutin, Rifametane, Rifamexil, Rifamide, Rifampin, Rifapentine, Rifaximin, Rolitetracycline, Rolitetracycline Nitrate, Rosaramicin, Rosaramicin Butyrate, Rosaramicin Propionate, Rosaramicin Sodium Phosphate, Rosaramicin Stearate, Rosoxacin, Roxarsone, Roxithromycin, Sancycline, Sanfetrinem Sodium, Sarmoxicillin, Sarpicillin, Scopafungin, Sisomicin, Sisomicin Sulfate, Sparfloxacin, Spectinomycin Hydrochloride, Spiramycin, Stallimycin Hydrochloride, Steffimycin, Sterile Ticarcillin Disodium, Streptomycin Sulfate, Streptonicozid, Sulbactam Sodium, Sulfabenz, Sulfabenzamide, Sulfacetamide, Sulfacetamide Sodium, Sulfacytine, Sulfadiazine, Sulfadiazine Sodium, Sulfadoxine, Sulfalene, Sulfamerazine, Sulfameter, Sulfamethazine, Sulfamethizole, Sulfamethoxazole, Sulfamonomethoxine, Sulfamoxole, Sulfanilate Zinc, Sulfanitran, Sulfasalazine, Sulfasomizole, Sulfathiazole, Sulfazamet, Sulfisoxazole, Sulfisoxazole Acetyl, Sulfisoxazole Diolamine, Sulfomyxin, Sulopenem, Sultamicillin, Suncillin Sodium, Talampicillin Hydrochloride, Tazobactam, Teicoplanin, Temafloxacin Hydrochloride, Temocillin, Tetracycline, Tetracycline Hydrochloride, Tetracycline Phosphate Complex, Tetroxoprim, Thiamphenicol, Thiphencillin Potassium, Ticarcillin Cresyl Sodium, Ticarcillin Disodium, Ticarcillin Monosodium, Ticlatone, Tiodonium Chloride, Tobramycin, Tobramycin Sulfate, Tosufloxacin, Trimethoprim, Trimethoprim Sulfate, Trisulfapyrimidines, Troleandomycin, Trospectomycin Sulfate, Trovafloxacin, Tyrothricin, Vancomycin, Vancomycin Hydrochloride, Virginiamycin, Zorbamycin.

Anti-viral agents can be isolated from natural sources or synthesized and are useful for killing or inhibiting the growth or function of viruses. Anti-viral agents are compounds which prevent infection of cells by viruses or replication of the virus within the cell. There are several stages within the process of viral infection which can be blocked or inhibited by anti-viral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleotide analogues), maturation of new virus proteins (e.g. protease inhibitors), and budding and release of the virus.

Anti-viral agents useful in the invention include but are not limited to: immunoglobulins, amantadine, interferons, nucleotide analogues, and protease inhibitors. Specific examples of anti-virals include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir;

Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

The interferons are cytokines which are secreted by virus-infected cells as well as immune cells. The interferons function by binding to specific receptors on cells adjacent to the infected cells, causing the change in the cell which protects it from infection by the virus. $\alpha$ and $\beta$-interferon also induce the expression of Class I and Class II MHC molecules on the surface of infected cells, resulting in increased antigen presentation for host immune cell recognition. $\alpha$ and $\beta$-interferons are available as recombinant forms and have been used for the treatment of chronic hepatitis B and C infection. At the dosages which are effective for anti-viral therapy, interferons have severe side effects such as fever, malaise and weight loss.

Anti-fungal agents are used to treat superficial fungal infections as well as opportunistic and primary systemic fungal infections. Anti-fungal agents are useful for the treatment and prevention of infective fungi. Anti-fungal agents are sometimes classified by their mechanism of action. Some anti-fungal agents function, for example, as cell wall inhibitors by inhibiting glucose synthase. These include, but are not limited to, basiungin/ECB. Other anti-fungal agents function by destabilizing membrane integrity. These include, but are not limited to, immidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g. chitinase) or immunosuppression (501 cream).

Anti-parasitic agents kill or inhibit parasites. Examples of anti-parasitic agents, also referred to as parasiticides, useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, timidazole, trimethroprim-sulfamethoxazole, and tryparsamide some of which are used alone or in combination with others.

In practicing certain methods of the present invention, it is required to obtain a level of gelsolin in a subject. This level then is compared to a predetermined value, wherein the level of gelsolin in comparison to the predetermined value is indicative of the likelihood that the subject will benefit from continued therapy. The subject then can be characterized in terms of the net benefit likely to be obtained from a change in therapy.

The level of the gelsolin for the subject can be obtained by any art recognized method. Typically, the level is determined by measuring the level of the marker in a body fluid, for example, blood, lymph, saliva, urine and the like. The level can be determined by ELISA, or immunoassays or other conventional techniques for determining the presence of the marker. Conventional methods include sending a sample(s) of a subject's body fluid to a commercial laboratory for measurement. Methods for measuring gelsolin are described in the Example.

The invention also involves comparing the level of gelsolin for the subject with a predetermined value. The predetermined value can take a variety of forms. It can be single cut-off value, such as a median or mean. It can be established based upon comparative groups, such as, for example, where the risk in one defined group is double the risk in another defined group. It can be a range, for example, where the tested population is divided equally (or unequally) into groups, such as a low-risk group, a medium-risk group and a high-risk group, or into quartiles, the lowest quartile being subjects with the highest risk and the highest quartile being subjects with the lowest risk, or into tertiles the lowest tertile being subjects with the highest risk and the highest tertile being subjects with the lowest risk.

The predetermined value can depend upon the particular population of subjects selected. For example, an apparently healthy population will have a different 'normal' range of gelsolin than will a population the subjects of which have had a prior infection or other condition. Accordingly, the predetermined values selected may take into account the category in which a subject falls. Appropriate ranges and categories can be selected with no more than routine experimentation by those of ordinary skill in the art.

The preferred body fluid is blood. One preferred predetermined value of gelsolin is about 2.4 µM/L of plasma.

An important predetermined value of gelsolin is a value that is the average for a healthy subject population (i.e., subjects who have no signs and symptoms of disease). The predetermined value will depend, of course, upon the characteristics of the subject population in which the subject lies. In characterizing risk, numerous predetermined values can be established.

Presently, there are commercial sources which produce reagents for assays for gelsolin. These include, for example, CYTOSKELETON (Denver, Colo.), SIGMA (St. Louis, Mo.) and CALBIOCHEM (San Diego, Calif.).

The invention further comprises measuring the level of gelsolin together with a level of another marker of infection such as, for example, a level white blood cells (WBCs) for characterizing a subject's risk of developing an infection. A level of gelsolin in the subject is obtained. The level of gelsolin is compared to a predetermined value to establish a first risk value. A level of WBCs in the subject is also obtained. The level of the WBCs in the subject is compared to a second predetermined value to establish a second risk value. The subject's risk profile of developing an infection then is characterized based upon the combination of the first risk value and the second risk value, wherein the combination of the first risk value and second risk value establishes a third risk value different from the first and second risk values. In some embodiments, the third risk value is greater than either of the first and second risk values. The preferred subjects for testing and predetermined values are as described above. The infection may be any infection such as described above.

The invention provides methods for determining whether a subject will benefit from continued therapy or would benefit from a change in therapy. The benefit is typically a reduction in the rate of occurrence of an infection or a faster recovery from an infection. Determining whether a subject will benefit from continued therapy or would benefit from a change in therapy is clinically useful. One example of clinical usefulness of the methods of this invention includes identifying subjects who are less likely or more likely to respond to a therapy. The methods of the invention are also useful in predicting or determining that a subject would benefit from continued therapy or would benefit from a change in therapy. Another example of clinical usefulness, in the case of human subjects for example, includes aiding clinical investigators in the selection for clinical trials of subjects with a high likelihood of obtaining a net benefit. It is expected that clinical investigators now will use the present invention for determining entry criteria for clinical trials.

A subject who would benefit from continued therapy is a subject whose on-therapy level of gelsolin reaches a certain predetermined value or whose level of gelsolin is increasing. Predetermined values of gelsolin are described above. A subject who would benefit from a change in therapy is a subject whose on-therapy level of the gelsolin did not reach a certain predetermined value or whose on-therapy level of gelsolin is not increasing.

As used herein, a "change in therapy" refers to an increase or decrease in the dose of the existing therapy, a switch from one therapy to another therapy, an addition of another therapy to the existing therapy, or a combination thereof. A switch from one therapy to another may involve a switch to a therapy with a high risk profile but where the likelihood of expected benefit is increased. In some embodiments, preferred therapies are therapies that increase the levels of gelsolin. A subject who would benefit from a change in therapy by increasing the dose of the existing therapy is a subject who, for example, was on the therapy but was not receiving the maximum tolerated dose or the maximum allowed dose of the therapy and whose level of gelsolin did not reach a certain predetermined value. In such instances the dose of the existing therapy is increased until the level of gelsolin reaches a certain predetermined value. In some instances, the dose of the existing therapy is increased from the existing dose to a higher dose that is not the maximum tolerated dose nor the maximum allowed dose of the therapy. In other instances, the dose is increased to the maximum tolerated or to the maximum allowed dose of the therapy. A subject who would benefit from a change in therapy by decreasing the dose of the existing therapy is, for example, a subject whose on-therapy level of gelsolin reaches or can reach a certain predetermined value with a lower dose of the therapy.

A subject who would benefit from a switch from one therapy to another therapy is, for example, a subject who was on the maximum tolerated dose or the maximum allowed dose of the therapy and whose level of gelsolin did not reach a certain predetermined value. Another example is a subject was not on the maximum tolerated or the maximum allowed dose of the therapy but was determined by a health care practitioner to more likely benefit from another therapy. Such determinations are based, for example, on the development in the subject of unwanted side effects on the initial therapy or a lack of response to the initial therapy.

A subject who would benefit from a change in therapy by the addition of another therapy to the existing therapy is, for example, a subject who was on a therapy but whose level of gelsolin did not reach a certain predetermined value. In such instances, another therapy is added to the existing therapy. The therapy that is added to the existing therapy can have a different mechanism of action in increasing the level of gelsolin than the existing therapy. In some instances, a combination of the aforementioned changes in therapy may be used.

The invention also provides methods for determining the efficacy of a therapy. The efficacy is typically the efficacy of the therapy in increasing the level of gelsolin. This is sometimes also referred to as a positive response or a favorable response. Efficacy can be determined by a gelsolin blood test(s) to determine whether gelsolin levels are increased as a result of therapy. In some embodiments efficacy determination is based on the efficacy of a therapy in increasing both gelsolin and normalizing WBCs counts.

The gelsolin measurement is reported in μM/L (micromoles/Liter), mg/dl (milligrams/deciliter), or mg/L (milligrams/Liter).

The invention also provides methods for deciding on the course of a therapy in a subject undergoing therapy to treat an infection. Such a course of therapy is decided on the basis of the level of gelsolin. Therapies for treating or reducing the risk of an infection are described above. In some embodiments, the subject already has had an infection or is at risk of having an infection. A subject who has had a primary (first) infection is at an elevated risk of a secondary (second) infection due to the primary infection. In some embodiments, the subject is at an elevated risk of an infection because the subject has one or more risk factors to have an infection. Examples of risk factors to have an infection are described above. In some embodiments, the subject who is at an elevated risk of an infection may be an apparently healthy subject. An apparently healthy subject is a subject who has no signs or symptoms of disease.

These methods have important implications for patient treatment and also for the clinical development of new therapies. It is also expected that clinical investigators now will use the present methods for determining entry criteria for human subjects in clinical trials. Health care practitioners select therapeutic regimens for treatment based upon the expected net benefit to the subject. The net benefit is derived from the risk to benefit ratio. The present invention permits the determination of whether a subject will benefit from continued therapy or would benefit from a change in therapy, thereby aiding the physician in selecting a therapy.

The amount of a treatment may be varied for example by increasing or decreasing the amount of gelsolin or pharmacological agent or a therapeutic composition, by changing the therapeutic composition administered, by changing the route of administration, by changing the dosage timing and so on. The effective amount will vary with the particular infection or condition being treated, the age and physical condition of the subject being treated, the severity of the infection or condition, the duration of the treatment, the nature of the concurrent therapy (if any), the specific route of administration, and like factors are within the knowledge and expertise of the health practitioner. For example, an effective amount can depend upon the degree to which an individual has been exposed to or affected by exposure to the infection.

An effective amount is a dosage of the therapeutic agent sufficient to provide a medically desirable result. An effective amount may also, for example, depend upon the degree to which an individual has abnormally decreased levels of gelsolin. It should be understood that the therapeutic agents of the invention are used to treat or prevent infections, that is, they may be used prophylactically in subjects at risk of developing an infection. Thus, an effective amount is that amount which can lower the risk of, slow or perhaps prevent altogether the development of an infection. It will be recognized when the therapeutic agent is used in acute circumstances, it is used to prevent one or more medically undesirable results that typically flow from such adverse events.

The factors involved in determining an effective amount are well known to those of ordinary skill in the art and can be addressed with no more than routine experimentation. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

The therapeutically effective amount of a pharmacological agent of the invention is that amount effective to treat the disorder, such as an infection. In the case of infections the desired response is inhibiting the progression of the infection. This may involve only slowing the progression of the infection temporarily, although more preferably, it involves halting the progression of the infection permanently. This can be monitored by routine diagnostic methods known to those of ordinary skill in the art. The desired response to treatment of the infection also can be delaying the onset or even preventing the onset of the infection.

The pharmacological agents used in the methods of the invention are preferably sterile and contain an effective amount of gelsolin for producing the desired response in a unit of weight or volume suitable for administration to a subject. The doses of pharmacological agents administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The dosage of a pharmacological agent may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days.

Various modes of administration are known to those of ordinary skill in the art which effectively deliver the pharmacological agents of the invention to a desired tissue, cell, or bodily fluid. The administration methods are discussed elsewhere in the application. The invention is not limited by the particular modes of administration disclosed herein. Standard references in the art (e.g., *Remington's Pharmaceutical Sciences*, 20th Edition, Lippincott, Williams and Wilkins, Baltimore Md., 2001) provide modes of administration and formulations for delivery of various pharmaceutical preparations and formulations in pharmaceutical carriers. Other protocols which are useful for the administration of pharmacological agents of the invention will be known to one of ordinary skill in the art, in which the dose amount, schedule of administration, sites of administration, mode of administration and the like vary from those presented herein.

Administration of pharmacological agents of the invention to mammals other than humans, e.g. for testing purposes or veterinary therapeutic purposes, is carried out under substantially the same conditions as described above. It will be understood by one of ordinary skill in the art that this invention is applicable to both human and animal diseases. Thus, this invention is intended to be used in husbandry and veterinary medicine as well as in human therapeutics.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

A pharmacological agent or composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the pharmacological agents of the invention, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds. The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well known in the art of pharmacy. All methods include the step of bringing the active agent into association with a carrier, which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, pills, lozenges, each containing a predetermined amount of the active compound (e.g., gelsolin). Other compositions include suspensions in aqueous liquids or non-aqueous liquids such as a syrup, elixir, an emulsion, or a gel.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of gelsolin or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), EUDRAGIT L30D, AQUATERIC, cellulose acetate phthalate (CAP), EUDRAGIT L, EUDRAGIT S, and SHELLAC. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, gelsolin may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are FAST-FLO, EMDEX, STA-Rx 1500, EMCOMPRESS and AVICELL.

Disintegrants may be included in the formulation of the therapeutic into a solid dosage form. Materials used as disintegrants include but are not limited to starch, including the commercial disintegrant based on starch, EXPLOTAB. Sodium starch glycolate, AMBERLITE, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, CARBOWAX 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of gelsolin either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of gelsolin. Gelsolin is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-γ and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the ULTRAVENT nebulizer, manufactured by Mallinckrodt, Inc., St. Louis, Mo.; the ACORN II nebulizer, manufactured by Marquest Medical Products, Englewood, Colo.; the VENTOLIN metered dose inhaler, manufactured by Glaxo Inc., Research Triangle Park, N.C.; and the SPINHALER powder inhaler, manufactured by Fisons Corp., Bedford, Mass.

All such devices require the use of formulations suitable for the dispensing of gelsolin. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified gelsolin may also be prepared in different formulations depending on the type of chemical modification or the type of device employed.

Formulations suitable for use with a nebulizer, either jet or ultrasonic, will typically comprise gelsolin dissolved in water at a concentration of about 0.1 to 25 mg of biologically active gelsolin per mL of solution. The formulation may also include a buffer and a simple sugar (e.g., for gelsolin stabilization and regulation of osmotic pressure). The nebulizer formulation may also contain a surfactant, to reduce or prevent surface induced aggregation of the gelsolin caused by atomization of the solution in forming the aerosol.

Formulations for use with a metered-dose inhaler device will generally comprise a finely divided powder containing the gelsolin suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing gelsolin and may also include a bulking agent, such as lactose, sorbitol, sucrose, or mannitol in amounts which facilitate dispersal of the powder from the device, e.g., 50 to 90% by weight of the formulation. The gelsolin should most advantageously be prepared in particulate form with an average particle size of less than 10 mm (or microns), most preferably 0.5 to 5 mm, for most effective delivery to the distal lung.

Nasal (or intranasal) delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

Gelsolin and optionally other therapeutics may be administered per se or in the form of a pharmaceutically acceptable salt.

The therapeutic agent(s), including specifically but not limited to gelsolin, may be provided in particles. Particles as used herein means nano or microparticles (or in some instances larger) which can consist in whole or in part of gelsolin or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the gelsolin in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug therefrom. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

The invention also contemplates the use of kits. In some aspects of the invention, the kit can include a pharmaceutical preparation vial, a pharmaceutical preparation diluent vial, and gelsolin. The vial containing the diluent for the pharmaceutical preparation is optional. The diluent vial contains a diluent such as physiological saline for diluting what could be a concentrated solution or lyophilized powder of gelsolin. The instructions can include instructions for mixing a particular amount of the diluent with a particular amount of the concentrated pharmaceutical preparation, whereby a final formulation for injection or infusion is prepared. The instructions may include instructions for treating a subject with an effective amount of gelsolin. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

The present invention is further illustrated by the following Example, which in no way should be construed as further limiting. The entire contents of all of the references (including literature references, issued patents, published patent applications, and co-pending patent applications) cited throughout this application are hereby expressly incorporated by reference.

EXAMPLE

Sepsis is associated with various biochemical abnormalities, including plasma gelsolin depletion. While the true function of plasma gelsolin is not known, clinical and animal studies have shown that depletion of plasma gelsolin by injury and inflammation associates with adverse outcomes. We examined plasma gelsolin in septic mice and found that plasma gelsolin depletion occurs after septic challenges and that significant depletion accompanies lethal sepsis. Repletion of plasma gelsolin leads to a more favorable cytokine profile and improves mortality. Plasma gelsolin has a physiologic role in systemic inflammation and gelsolin replacement may represent a new therapy for infections and sepsis.

Gelsolin, specifically cytoplasmic gelsolin (cGSN), first discovered as an intracellular actin-binding protein involved in cell motility (Yin, H. L. & Stossel, T. P. (1979) *Nature* 281, 583-6) is also an abundant secretory protein (Yin, H. L., Kwiatkowski, D. J., Mole, J. E. & Cole, F. S. (1984) *J Biol Chem* 259, 5271-6). The exported isoform of gelsolin, designated plasma gelsolin (pGSN), has 25 additional amino acids and originates from alternative splicing of a single gene (Kwiatkowski, D. J., Stossel, T. P., Orkin, S. H., Mole, J. E., Colten, H. R. & Yin, H. L. (1986) *Nature* 323, 455-8). Although postulated as an "actin-scavenger" (Lee, W. M. & Galbraith, R. M. (1992) *N Engl J Med* 326, 1335-41), pGSN's biologic function is a mystery. pGSN's prevalence in complex organisms, including *drosophila* (Stella, M. C., Schauerte, H., Straub, K. L. & Leptin, M. (1994) *J Cell Biol* 125, 607-16), is consistent with it having an important physiologic role. In humans, trauma, massive hemolysis, acute respiratory distress syndrome (ARDS), hematopoeitic stem cell transplantation (HSCT), acute hepatic failure, myonecrosis, pancreatitis, and sepsis can lead to pGSN depletion (Dahl, B., Schiodt, F. V., Ott, P., Gvozdenovic, R., Yin, H. L. & Lee, W. M. (1999) *Shock* 12, 102-4; Suhler, E., Lin, W., Yin, H. L. & Lee, W. M. (1997) *Crit Care Med* 25, 594-8; DiNubile, M. J., Stossel, T. P., Ljunghusen, O. C., Ferrara, J. L. & Antin, J. H. (2002) *Blood* 100, 4367-71; and Lind, S. E., Smith, D. B., Janmey, P. A. & Stossel, T. P. (1988) *Am Rev Respir Dis* 138, 429-34). Furthermore, in trauma patients and HSCT recipients, lower pGSN levels predict increased morbidity and mortality (DiNubile, M. J., Stossel, T. P., Ljunghusen, O. C., Ferrara, J. L. & Antin, J. H. (2002) *Blood* 100, 4367-71; Mounzer, K. C., Moncure, M., Smith, Y. R. & Dinubile, M. J. (1999) *Am J Respir Crit Care Med* 160, 1673-81).

In animals, burns and acute lung injury induced by oxidative stress, radiation and hyperoxia also cause pGSN depletion (Rothenbach, P. A., Dahl, B., Schwartz, J. J., O'Keefe, G. E., Yamamoto, M., Lee, W. M., Horton, J. W., Yin, H. L. & Turnage, R. H. (2004) *J Appl Physiol* 96, 25-31; Christofidou-Solomidou, M., Scherpereel, A., Solomides, C. C., Christie, J. D., Stossel, T. P., Goelz, S. & DiNubile, M. J. (2002) *J Investig Med* 50, 54-60; and Christofidou-Solomidou, M., Scherpereel, A., Solomides, C. C., Muzykantov, V. R., Machtay, M., Albelda, S. M. & DiNubile, M. J. (2002) *Lung* 180, 91-104). Administration of pGSN to some of these animals lessens the injuries (Rothenbach, P. A., Dahl, B., Schwartz, J. J., O'Keefe, G. E., Yamamoto, M., Lee, W. M., Horton, J. W., Yin, H. L. & Turnage, R. H. (2004) *J Appl Physiol* 96, 25-31; and Christofidou-Solomidou, M., Scherpereel, A., Solomides, C. C., Christie, J. D., Stossel, T. P., Goelz, S. & DiNubile, M. J. (2002) *J Investig Med* 50, 54-60).

We hypothesized that if systemic inflammation associated with sepsis depresses pGSN, restoration of pGSN could be beneficial. Here, we show that pGSN levels fall in mice subjected to endotoxemia or peritonitis, and repletion of pGSN leads to improved survival and cytokine profile shift in septic mice.

Materials and Methods

Animals

Wild type C57BL/6 male mice were purchased from CHARLES RIVER LABORATORIES (Wilmington, Mass.). Toll-like receptor 4 (TLR4) mutants C3H/HeJ male mice were purchased from the JACKSON LABORATORY (Bar Harbor, Me.). Mice were given free access to a standard feed and water and all procedures and studies described here have been approved by Harvard Medical Area Standing Committee on Animals according to standards as set forth in The Guide for the Care and Use of Laboratory Animals.

LPS Dose Response 6-8 week old male C57BL/6 mice weighing 18-20 g were injected intraperitoneally (i.p.) with LPS (*Pseudomonas aeruginosa* Serotype 10, from SIGMA (St. Louis, Mo.) at doses of 0, 10, 20, and 40 mg/kg in 100 µl of phosphate buffered saline (PBS), and 3-4 were used in each group. 24 hours after LPS administration, animals were anesthetized with 0.015-0.017 mg/g AVERTIN i.p. (FLUKA CHEMIE, Buchs, Switzerland). Blood was then collected by retroorbital bleeding into 0.1 volume of Aster-Jandl anticoagulant solution (Gamulescu, M. A., Seifert, K., Tingart, M., Falet, H. & Hoffmeister, K. M. (2003) *Platelets* 14, 211-7) and centrifuged at 1000×g for 10 minutes to generate plasma. Plasma was frozen in liquid nitrogen and stored at −80° C.

Murine Sepsis by CLP (Cecal Ligation and Puncture)

8-10 week old male C57BL/6 mice were first anesthetized with 0.015-0.017 mg/g i.p. RAVERTIN. The cecum of each anesthetized animal was exposed thru a small incision in the lower anterior abdomen, and punctured by a 19-gauge needle. A small amount of intestinal content was extruded and the cecum was ligated without obstructing intestinal tract with 6-0 silk suture. After replacing the intestinal contents, the abdomen was closed with a 4-0 silk suture. For pGSN level study, the 5 animals received 1 ml of PBS subcutaneously immediately after surgery. Five animals that did not undergo CLP served as controls. Animals were allowed to recover with free access to food and water. 24 hours after CLP, animals were then anesthetized and plasma collected as described before. In addition, heart, lungs, liver, kidneys and skeletal muscles from hind leg were harvested and frozen at −80° C. from each animal. Lungs were harvested after perfusion by first puncturing the right ventricle of the heart and injecting 1 ml of PBS into the left ventricle. For the mortality study, 20 animals were subjected to CLP and 10 animals received subcutaneous (s.c.) injections of 1 ml of 1) 150 mM NaCl (saline) or 2) 8 mg/ml of recombinant human pGSN (BIOGEN, Boston, Mass.) with 0.4 mM Ca in saline immediately and 24 hours after CLP.

LPS Mortality and Plasma Cytokines 6-8 week old male C57BL/6 mice weighing 18-20 g were injected i.p. with 25 mg/kg LPS (*Escherichia coli* O55:B5, St. Louis, SIGMA) and divided to receive 400 μl dorsal subcutaneous injection of 1) pGSN: 20 mg/ml of recombinant human pGSN with 1 mM Ca in saline (8 animals), 2) BSA: 20 mg/ml of bovine serum albumin (SEROLOGICALS, Norcross, Ga.) with 1 mM Ca in saline (9 animals), or 3) saline: sterile saline alone (9 animals), immediately, and at 24, 48, and 72 hours after LPS injections. The animals were monitored frequently and mortality was recorded for 7 days. Surviving mice were euthanized. In a separate experiment, mice received the same LPS challenge and were divided to receive pGSN or saline treatment as described and sacrificed for plasma and organ collections at 6 hours (5 mice per treatment group) and 24 hours (4 mice per treatment group) post LPS challenge. In addition, control mice without LPS challenge were given only s.c. saline (5 mice) or pGSN (3 mice) 24 hours prior to being sacrificed for blood and organ harvesting. Plasma and organs were collected from each mouse as described.

pGSN in LPS-Resistant Mice 6-8 week old male C3H/Hej mice weighing 19-20 g were injected i.p. with 25 mg/kg *E. coli* LPS (4 mice) and unchallenged mice served as controls (4 mice). 24 hours after LPS challenge, plasma samples were collected from anesthetized mice as described above. Gelsolin level was measured in each plasma sample.

Mouse Cytokine Measurements

Plasma GM-CSF, INF-γ, IL-1β, IL-6, IL-10, and TNF-α cytokines were measured using ELISA assays (LINCO Research, St. Charles, Mo.). The lower range of the assay is <3.2 pg/ml for each cytokine, and levels ≤3.2 pg/ml were assigned a value of zero.

Gelsolin and Albumin Measurements

Plasma gelsolin was measured in duplicate samples by its ability to stimulate actin nucleation (Janmey, P. A., Chaponnier, C., Lind, S. E., Zaner, K. S., Stossel, T. P. & Yin, H. L. (1985) *Biochemistry* 24, 3714-23). Mouse plasma was diluted 1:5 fold in 0.1 M KCl, 0.2 mM $MgCl_2$, 1 mM EGTA, 0.5 mM ATP, 0.5 mM β-mercaptoethanol, 10 mM TRIS-HCl buffer, pH 7.4 (Buffer B). Of the diluted plasma sample, 5 μl was added to 280 μl Buffer B supplemented with 1.5 mM $CaCl_4$ and 0.4 μM PHALLACIDIN in 6×50 mm borosilicate culture tubes. The actin polymerization reaction was initiated by adding 15 μl 20 μM pyrene actin in 0.5 mM ATP, 5 mM β-mercaptoethanol, 0.2 mM $CaCl_2$, 0.2 mM TRIS-HCl buffer, pH 7.4 (Buffer A). Polymerization was monitored for 200 seconds in a spectrofluorimeter at excitation and emission wavelengths of 366 and 386 nm respectively. Gelsolin concentrations were estimated from a standard curve using recombinant human pGSN. Stock pyrene actin for these assays, prepared by the method of Kouyama and Mihashi (Kouyama, T. & Mihashi, K. (1981) *Eur J Biochem* 114, 33-8), was stored at −80° C. in lots, thawed and diluted 10× with Buffer A, centrifuged at 250,000×g for 30 minutes after standing overnight.

Gelsolin quantification by the actin nucleation assay correlates well with levels obtained from Western blotting measurements (Mounzer, K. C., Moncure, M., Smith, Y. R. & Dinubile, M. J. (1999) *Am J Respir Crit Care Med* 160, 1673-81). The assay is a highly specific, as evidenced by virtually zero activity in plasma of LPS treated gelsolin-null mice (data not shown); however, the assay does not discriminate between cGSN and pGSN. It is also not species-specific and is thus able to approximate total gelsolin levels in mice treated with recombinant human pGSN. Lipids complexing to pGSN do not affect pGSN's actin nucleation activity (Janmey, P. A., Iida, K., Yin, H. L. & Stossel, T. P. (1987) *J Biol Chem* 262, 12228-36).

Albumin levels were measured colorimetrically using a commercial kit (STANBIO, Boerne, Tex.) according to the manufacture's instruction.

Protein Extraction from Organs

Organs collected 6 hr after being challenged with 25 mg/kg i.p. *E coli* LPS, or CLP were analyzed. Organs from unchallenged mice served as controls. Each organ was homogenized in RIPA buffer (BOSTON BIOPRODUCTS, Ashland, Mass.), supplemented with protein inhibitor cocktail (CALBIOCHEM, La Jolla, Calif.) at 1:100 concentration and sodium orthovanadate and incubated on ice for 30 minutes before centrifugation at 2,000×g for 30 minutes at 4° C. The supernatant was removed and centrifuged again at 10,000×g for 30 minutes at 4° C. The supernatant was removed and kept at −80° C. till analysis.

Western Blot Analysis

Protein concentration was determined for each sample using DC Protein Assay (Bio-Rad, Hercules, Calif.) following the manufacturer's instructions. 10 μg of each sample was heated at 85° C. for 3 minutes in SDS-sample buffer (BOSTON BIOPRODUCTS) then analyzed by SDS-PAGE using 12% TRIS-Glycine Gel (INVITROGEN, Carlsbad, Calif.) and transferred to a PVDF membrane (MILLIPORE, Bedford, Mass.). After blocking the membrane overnight in 5% non-fat dry milk in TRIS-buffered saline (TBS) with 0.05% TWEEN 20, mouse pGSN anti-sera was added at 1:1000 and then probed with HRP-linked anti-rabbit IgG's (CELL SIGNALING, Beverly, Mass.) at 1:2000. Chemiluminescence was developed with LumiGLO (CELL SIGNALING, Beverly, Mass.) and photofilm was exposed and developed. The anti-mouse pGSN sera was produced by immunizing rabbits against a peptide derived from the plasma extension of mouse pGSN using a commercial service (INVITROGEN, Carlsbad, Calif.). The specificity and sensitivity of the anti-sera has been tested using ELISA and Western Blotting shown to be specific against only mouse pGSN and not cytoplasmic gelsolin (cGSN) (Data not shown).

Gelsolin-LPS Binding

All studies were done in duplicates. Each well of a MICROLITE 2, white 96-well flat-bottom plate (DYNEX TECHNOLOGIES, Chantilly, Va.) was coated with various amount of recombinant human pGSN or BSA and incubated at 4° C. overnight. After 4 washes with PB buffer (145 mM NaCl, 5 mM KCl, 2 mM $MgCl_2$, 3.5 mM $NaH_2PO_4$, 10 mM glucose, 10 mM HEPES, 3 mg/ml BSA, 1 mM $CaCl_2$, pH 7.4), 2 μg of ALEXA488-labeled LPS (*Escherichia coli* serotype O55:B5, Molecular Probes, Eugene, Oreg.) was added to each well with 100 μl PB buffer and incubated at room temperature for 1 hour. After 4 washes with PB buffer, fluorescence of each well was analyzed in a spectrofluorimeter at excitation and emission wavelengths of 488 and 520 nm respectively. Amount of ALEXA488-LPS bound was estimated by extrapolating from a standard curve generated by seeding various amounts of ALEXA488-LPS in PB buffer.

LPS Stimulation of Monocytic Cells

Human monocytic cell line THP-1 was purchased from American Type Culture Collection, Manassas, Va. Cells were maintained in RPMI (GIBCO, Grand Island, N.Y.) supplemented with 10% fetal bovine serum and 2% penicillin-streptomycin (GIBCO) at 37° C. 50,000 cells were seeded into each well in a 24-well plate and stimulated with or without 100 ng $E.$ $coli$ LPS and treated with 200 μg/ml human recombinant pGSN or BSA. 2 hours after LPS, 200 μl of media was collected and cells were removed by centrifugation at 1000×g for 10 minutes. TNF-α levels of cell-free media were determined by ELISA (R&D SYSTEMS, Minneapolis, Minn.).

Statistics.

Values are presented as mean±SD. A nonparametric test, the Spearman Rank Correlation was used to analyze correlations in the dose response study. Animal mortality is presented as Kaplan-Meier curves, and the log-rank test was used to analyze treatment impact on animal mortality. The Mann-Whiney U test was used to evaluate differences between cytokine and pGSN levels. A P value less than 0.05 was considered significant.

Results pGSN Levels Decrease in Mice Subjected to LPS or CLP

FIG. 1A shows that injection of increasing non-lethal doses of *Pseudomonas* LPS led to a progressive decrease, maximal at a dose of 20 mg/kg, of pGSN levels in mice (P<0.05). Plasma albumin levels did not alter with LPS treatment. Similarly, pGSN levels fell (P<0.001) while albumin levels increased (P=0.02) in mice after CLP. These data suggest that systemic inflammation due to sepsis has a specific affect on pGSN.

Figure 2A:
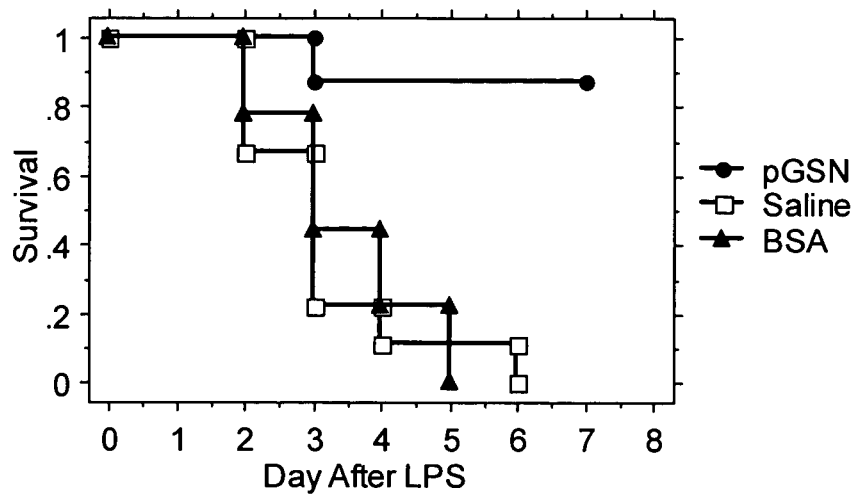
FIG. 2 is a plot of survival in septic mice. (A) In mice challenged with lethal LPS, those treated with pGSN had significantly better survival compared to BSA ($P<0.001$) or saline treated mice ($P<0.001$). (B) Mice subjected to CLP had similar favorable response to pGSN and had much better survival ($P=0.001$).
Figure 2B:
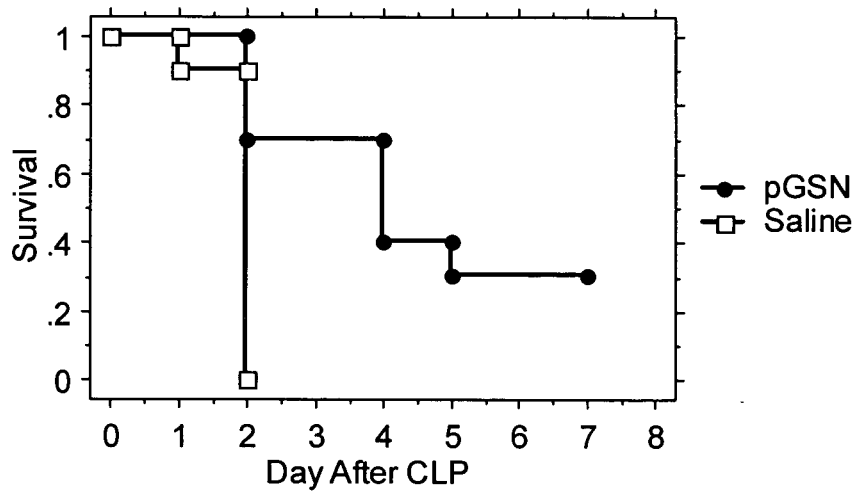

Repletion of pGSN Improved Survival in Septic Mice $E.$ $coli$ LPS at a dose of 25 mg/kg i.p. induces >90% mortality in mice within 7 days of injection, and the surviving mice appear completely recovered and exhibit no signs of distress. As shown in FIG. 2A, administration of exogenous pGSN at the time of LPS challenge significantly enhanced survival in endotoxemic mice compared to those treated with saline (P<0.001), or BSA (P<0.001). FIG. 2B shows that mice received pGSN also had significantly better survival than those received saline after CLP (P=0.001).

Figure 3:
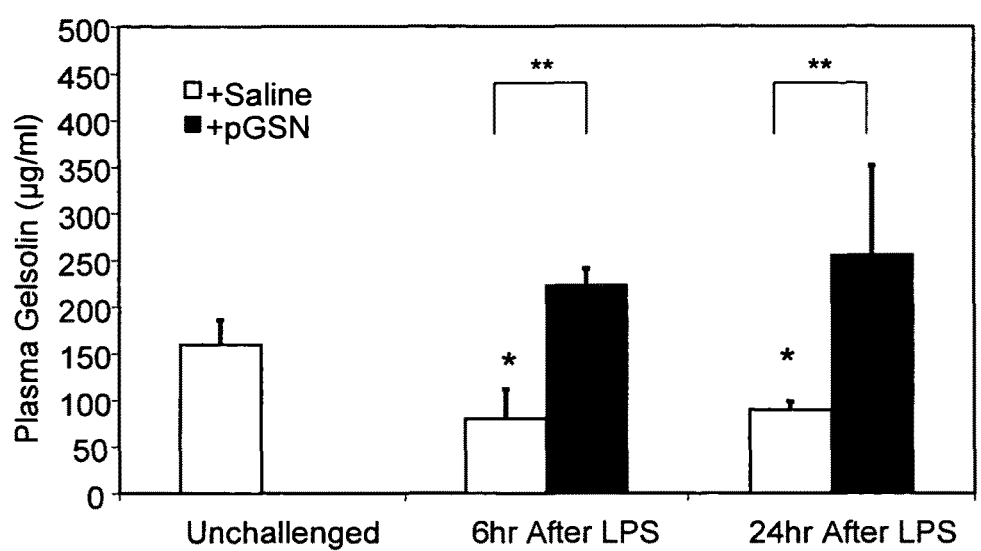
FIG. 3 is a graph of the pGSN levels in lethal endotoxemic mice treated with or without exogenous pGSN. Open bars denote mice received saline treatment and solid bars denote mice received exogenous pGSN treatment. Endogenous pGSN levels dropped to near 50% of normal within 6 hours of lethal LPS challenge and persisted for at least 24 hours ($*P<0.015$, compared with unchallenged mice). Administration of exogenous pGSN at the time of LPS challenge successfully raised pGSN levels ($**P<0.021$, comparing pGSN treated and untreated mice within the same group).

Administration of Exogenous pGSN Effectively Raised pGSN Levels in Endotoxemic Mice FIG. 3 shows the level of pGSN in mice challenged with lethal dose of $E.$ $coli$ LPS. In contrast to non-lethal *Pseudomonas* LPS which only caused pGSN to drop by 14%, a lethal does of $E.$ $coli$ LPS induced a 50% drop in pGSN level within 6 hours of LPS challenge. Subcutaneous injection of 8 mg recombinant pGSN successfully kept pGSN at or above the normal range in endotoxemic mice.

Effects of pGSN Repletion on the Cytokine Profiles of Endotoxemic Mice

Figure 4A:
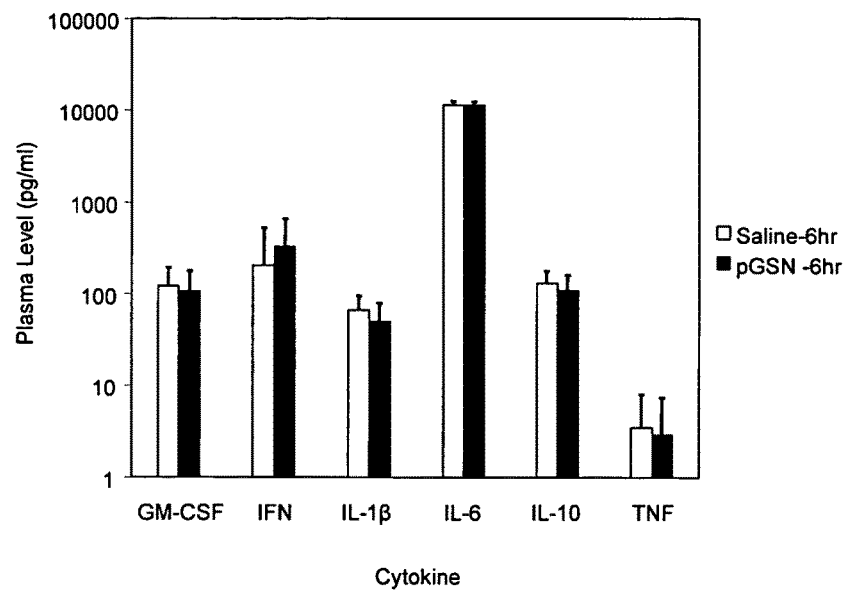
FIG. 4 is a graph of the cytokine profiles of endotoxemic mice treated with or without pGSN at 6 hr and 24 hr after LPS (y-axis in log scale). (A) Cytokine profiles did not differ between pGSN treated (solid bars) and untreated (open bars) mice 6 hours after LPS challenge. (B) However, 24 hours after LPS, saline-treated mice had significantly higher levels of GM-CSF, IFN-$\gamma$, and IL-1$\beta$ ($P<0.03$ for all) by as much as 10 folds compared to pGSN-treated mice. In contrast, IL-10 level was significantly higher in pGSN-treated mice ($P<0.03$).

We examined if administration of pGSN alters the cytokine profile of endotoxemic mice. FIG. 4A shows no differences in the plasma cytokine profile between pGSN-treated and saline-treated endotoxemic mice at 6 hours after LPS (P>0.05 for all cytokines shown). TNF-α levels were near baseline, consistent with published reports showing TNF-α peaks and begins to fall within 2-3 hours of LPS challenge in mice (Villa, P., Sartor, G., Angelini, M., Sironi, M., Conni, M., Gnocchi, P., Isetta, A. M., Grau, G., Buurman, W., van Tits, L. J. & et al. (1995) *Clin Diagn Lab Immunol* 2, 549-53).

Figure 4B:
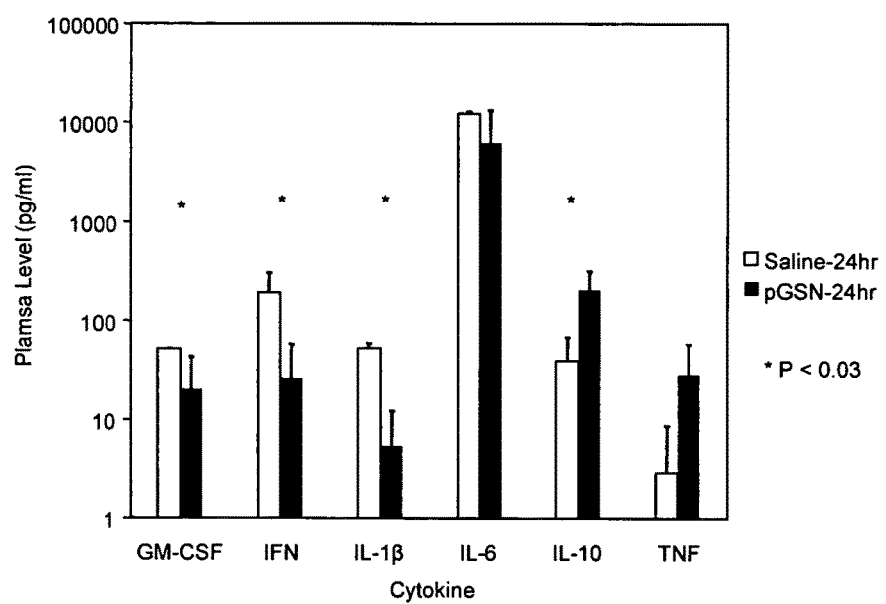

24 hours after LPS challenge, however, pGSN-treated mice had significantly lower levels of several pro-inflammatory cytokines (GM-CSF, IFN-γ, IL-1β), although IL-6 and TNF-α levels were not detectably different (FIG. 4B). In addition, pGSN treatment resulted in a significantly higher IL-10 level. pGSN does not appear to directly stimulate IL-10 secretion as unchallenged mice with or without pGSN administration did not have significantly different cytokine profiles; specifically, IL-10 was not increased in pGSN-treated unchallenged mice (Data not shown).

Tissue Distribution of pGSN

Figure 6:
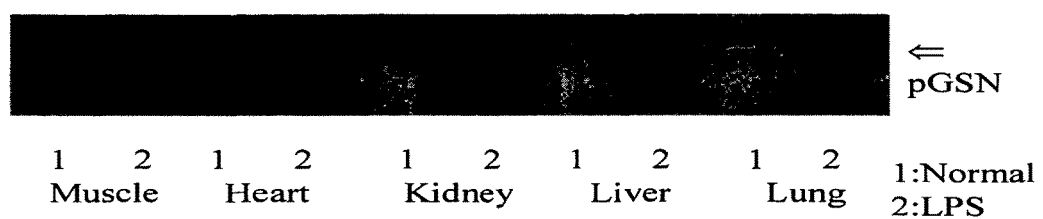
FIG. 6 is a Western blot analysis, staining for pGSN, on tissue extracts of mice challenged with or without LPS. The blot shows that lung has the highest concentration of pGSN comparing to skeletal muscle, heart, kidney, and liver in both normal and endotoxemic mice.

A representative Western blot analysis of skeletal muscles, hearts, kidneys livers, and lungs harvested from mice 6 hours after being treated with or without 25 mg/kg $E.$ $coli$ LPS, using mouse pGSN anti-sera is shown in FIG. 6. We found that lung has the highest concentration of pGSN in both normal and endotoxemic states. Since lungs were perfused with PBS to remove intravascular blood prior to harvesting, it is unlikely that blood contamination explains our result. We found similar tissue distribution of pGSN in mice subjected to CLP (Data not shown).

pGSN Binds LPS but does not Inhibit LPS Activating Monocytes

Figure 7:
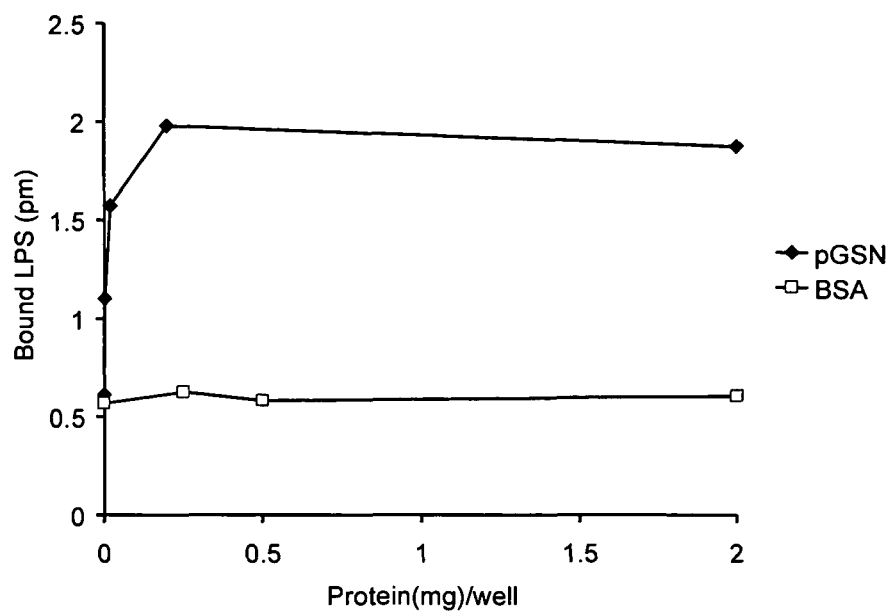
FIG. 7 is a plot comparing binding to LPS of pGSN vs BSA. Fluorescent-based binding study of pGSN and LPS showing a classic binding curve of fluorescent LPS plateauing at 250 μg/well of pGSN. BSA, serving as the control, protein showed minimal affinity to LPS.
Figure 8:
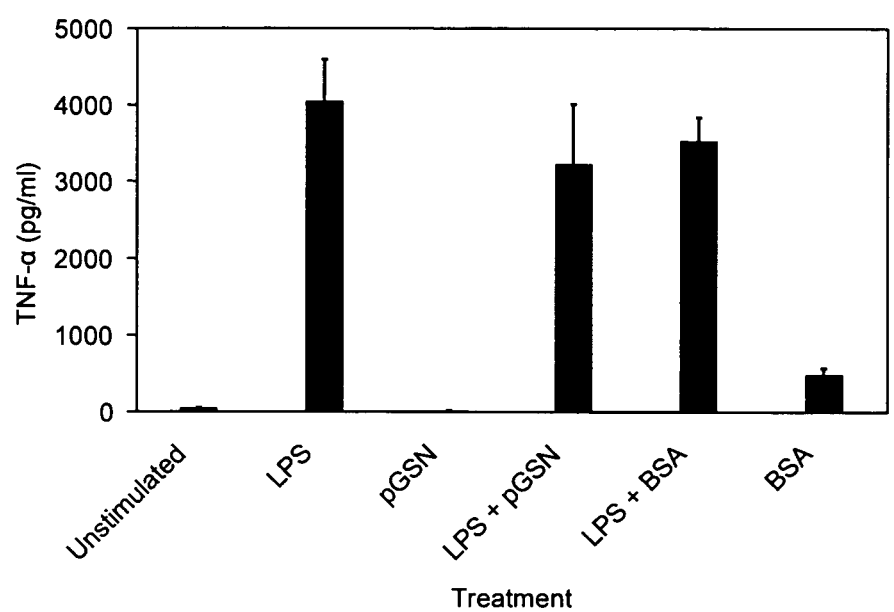
FIG. 8 is a graph of TNF-$\alpha$ levels of media from THP-1 cells treated without LPS (unstimulated), LPS only, pGSN only, LPS and pGSN, LPS and BSA, and BSA only. LPS stimulated THP-1 cells treated with pGSN or BSA had similar levels of TNF-$\alpha$ ($P>0.05$).

Since pGSN can bind bioactive lipids such as lysophosphatidic acid (Goetzl, E. J., Lee, H., Azuma, T., Stossel, T. P., Turck, C. W. & Karliner, J. S. (2000) *J Biol Chem* 275, 14573-8), we explored the possibility that pGSN can also bind LPS. FIG. 7 shows that pGSN specifically binds to fluorescent LPS while control protein, BSA, exhibited little affinity for LPS. However, pGSN does not appear to interfere with LPS's ability to elicit TNF-α secretion from human monocytes since LPS-stimulated THP-1 cells treated with pGSN or BSA secreted similar amount of TNF-α into the culture media (FIG. 8).

pGSN is Unaffected in TLR4-Mutant Mice Challenged with LPS

Figure 5:
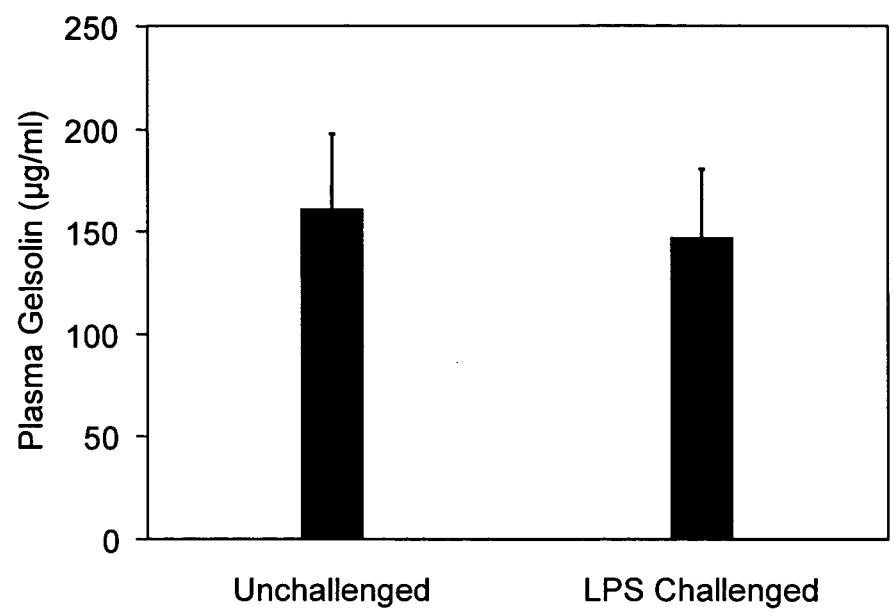
FIG. 5 is a graph of plasma gelsolin levels in *E. coli* LPS-challenged and unchallenged C3H/HeJ mice. LPS had no effect on pGSN levels of TLR4 mutants. C3H/HeJ mice injected with LPS that was lethal to C57BL/6 mice did not exhibit any signs of illness and had unaltered pGSN levels.

To examine if LPS directly causes pGSN depletion, we studied pGSN levels in C3H/HeJ mice, a strain expressing mutated TLR4 that renders the mice resistant to LPS-induced inflammation (Beutler, B. & Poltorak, A. (2001) *Crit Care Med* 29, S2-6; discussion S6-7). FIG. 5 shows that pGSN levels did not differ significantly between $E$ $coli$ LPS-challenged and unchallenged C3H/HeJ mice. Consistent with their known resistance to LPS, C3H/HeJ mice also appeared completely normal after LPS challenge.

Discussion

We have demonstrated here that significant pGSN depletion occurs after septic insult by endotoxin or peritonitis, and that exogenous pGSN dramatically improves the survival of septic mice. These data indicate that pGSN serves an important pro-survival function in sepsis.

The hypothesis of pGSN being an "actin-scavenger" stems from studies on cytoplasmic gelsolin (cGSN), and on one report demonstrating infusion of actin molecules into rats causing death. However, pGSN may not act as a scavenger for circulating actin in sepsis because early sepsis is not known to lead to actin release, and we have not been able to demonstrate gelsolin-actin complexes in the plasma of endotoxemic mice (unpublished data).

We explored the possibility that pGSN functions by directly interacting with LPS. Although pGSN can bind LPS, we found no evidence of pGSN interfering with LPS's ability to initiate inflammation in culture cells. Although pGSN was injected into mice immediately after LPS challenge, there was a delay in pGSN being delivered into the circulation due to subcutaneous route of administration. Therefore, it is unlikely that pGSN functions by direct LPS interference, and the early cytokine profiles of treated and untreated endotoxemic mice support this conclusion. It is possible that pGSN's ability to bind LPS alters a later event in LPS-induced inflammatory response. The similar early phase cytokine profiles of our control and pGSN-treated mice also suggest that pGSN is unlikely to function by interfering with early cytokine signaling, specifically TNF-α, since TNF-α inhibition in murine model of endotoxemia lowers plasma IL-1β and IL-6 levels within 3-4 hours of LPS challenge (Fong, Y., Tracey, K. J., Moldawer, L. L., Hesse, D. G., Manogue, K. B., Kenney, J. S., Lee, A. T., Kuo, G. C., Allison, A. C., Lowry, S. F. & et al. (1989) *J Exp Med* 170, 1627-33). On the other hand, cytokine profiles of treated and untreated mice 24 hours after LPS shows that pGSN is able to decrease several pro-inflammatory cytokines by as much as 90% while up-regulating IL-10, a cytokine believed to have an anti-inflammatory role in sepsis and inflammation (Moore, K. W., de Waal Malefyt, R., Coffman, R. L. & O'Garra, A. (2001) *Annu Rev Immunol* 19, 683-765). Since lethal dose of LPS is associated with persistently elevated pro-inflammatory cytokines, such as IL-1β and IFN-γ (Joshi, V. D., Kalvakolanu, D. V., Hebel, J. R., Hasday, J. D. & Cross, A. S. (2002) *Infect Immun* 70, 6896-903), we believe that the cytokine profile shift is consistent with pGSN promoting the resolution of inflammation.

Lung appears to have the highest concentration of pGSN compared to other organs by Western blot analysis, and may be the principle source of pGSN. This is in contrast to a previous study concluding that skeletal muscle as the main source of pGSN using Northern blot analysis (Kwiatkowski, D. J., Mehl, R., Izumo, S., Nadal-Ginard, B. & Yin, H. L. (1988) *J Biol Chem* 263, 8239-43). The contradiction may be due to the limited quantifying capability of Northern blot analysis or mRNA expression being not representative of protein production.

The lack of pGSN changes in LPS-resistant mice suggests that pGSN depletion is downstream to LPS activation of TLR4 and requires the initiation of the inflammatory cascade. However, the current study does not elucidate the mechanism of pGSN depletion in sepsis.

Since the discovery of gelsolin more than 20 years ago, majority of research have focused on cGSN and its interaction with actin (Kwiatkowski, D. J. (1999) *Curr Opin Cell Biol* 11, 103-8), and pGSN has received little attention. Our study shows that pGSN plays a critical role in systemic inflammation and administration of pGSN improves survival in murine sepsis and promotes a shift of cytokines toward the resolution of inflammation.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method for treating an infection in a subject having an infection comprising:
administering to a subject having an infection and in need of an increased blood level of gelsolin for the treatment of the infection an effective amount of cytoplasmic gelsolin (cGSN) or plasma gelsolin (pGSN) to increase the blood level of gelsolin to treat the infection, wherein the infection is caused by a gram-positive bacterium, an acid-fast *bacillus*, a spirochete, an actinomycete, a virus, a fungus, a parasite, *Ureaplasma* species, *Mycoplasma* species, *Chlamydia* species, or *Pneumocystis* species.

2. The method of claim 1, wherein the gelsolin is pGSN.

3. The method of claim 1, wherein the gram-positive bacterium is selected from the group consisting of *Staphylococcus* species, *Streptococcus* species, *Bacillus anthracis*, *Corynebacterium* species, *Diphtheroids* species, *Listeria* species, *Erysipelothrix* species and *Clostridium* species.

4. The method of claim 1, wherein the acid-fast *bacillus* is a *Mycobacterium* species.

5. The method of claim 1, wherein the spirochete is selected from the group consisting of *Treponema* species, *Borrelia* species, and *Leptospira* species.

6. The method of claim 1, wherein the virus is selected from the group consisting of Retro viruses, human immunodeficiency viruses, Cytomegaloviruses, Picorna viruses, Polio viruses, hepatitis A virus, enteroviruses, Coxsackie viruses, rhinoviruses, echoviruses, Calciviruses, Toga viruses, equine encephalitis viruses, rubella viruses, Flaviviruses, dengue viruses, encephalitis viruses, yellow fever viruses, coronaviruses, Rhabdoviruses, vesicular stomatitis viruses, rabies viruses, Filoviruses, ebola virus, Paramyxo viruses, parainfluenza viruses, mumps virus, measles virus, respiratory syncytial virus, Orthomyxoviruses, influenza viruses, Hantaan viruses, bunga viruses, phleboviruses, Nairo viruses, Arena viruses, hemorrhagic fever viruses, reoviruses, orbiviruses, rotaviruses, Birnaviruses, Hepadnaviruses, Hepatitis B virus, parvoviruses, Papovaviruses, papilloma viruses, polyoma viruses, Adenoviruses, Herpes viruses, varicella zoster virus, Pox viruses, variola viruses, vaccinia viruses, Iridoviruses, African swine fever viruses, delta hepatitis virus, non-A, non-B hepatitis virus, Hepatitis C, Norwalk viruses, astroviruses, and unclassified viruses.

7. The method of claim 1, wherein the fungus is selected from the group consisting of *Cryptococcus* species, *Histoplasma* species, *Coccidioides* species, *Paracoccidioides* species, *Blastomyces* species, *Chlamydia* species, *Candida* species, *Sporothrix* species, *Aspergillus* species, and fungi of mucormycosis.

8. The method of claim 1, wherein the parasite is selected from the group consisting of *Plasmodium* species, *Toxoplasma* species, *Babesia* species, *Leishmania* species, and *Trypanosoma* species.

9. The method of claim 1, wherein the gelsolin is administered orally, sublingually, buccally, intranasally, intravenously, intramuscularly, intrathecally, intraperitoneally, subcutaneously, intradermally, topically, rectally, vaginally, intrasynovially or intravitreously.

10. A method for treating an infection in a subject having a gram-negative bacterial infection comprising:
administering to a subject having a gram-negative bacterial infection and in need of an increased blood level of gelsolin for the treatment of the infection an effective amount of cytoplasmic gelsolin (cGSN) or plasma gelsolin (pGSN) to increase the blood level of gelsolin to treat the gram-negative bacterial infection, at a time subsequent to exposure to the infection.

11. The method of claim 10, wherein the gram-negative bacterial infection is caused by *Neisseria* species, *Branha-* mella species, *Escherichia* species, *Enterobacter* species, *Proteus* species, *Pseudomonas* species, *Klebsiella* species, *Salmonella* species, *Shigella* species, *Serratia* species, *Acinetobacter* species, *Haemophilus* species, *Brucella* species, *Yersinia* species, *Francisella* species, *Pasteurella* species, *Vibrio cholerae, Flavobacterium* species, *Pseudomonas* species, *Campylobacter* species, *Bacteroides* species, *Fusobacterium* species, *Calymmatobacterium* species, *Streptobacillus* species, or *Legionella* species.

12. The method of claim 10, wherein the gelsolin is pGSN.

13. The method of claim 10, wherein the gelsolin is administered orally, sublingually, buccally, intranasally, intravenously, intramuscularly, intrathecally, intraperitoneally, subcutaneously, intradermally, topically, rectally, vaginally, intrasynovially, or intravitreously.

14. The method of claim 10, wherein the gelsolin is administered at least about one hour after exposure to the infection.

15. A method for treating a subject having an infection comprising:
administering cytoplasmic gelsolin (cGSN) or plasma gelsolin (pGSN) with a therapeutic agent to a subject having an infection and in need of an increased blood level of gelsolin, in an effective amount to treat the infection, wherein the infection is caused by a gram-positive bacterium, a gram-negative bacterium, an acid-fast *bacillus*, a spirochete, an actinomycete, a virus, a fungus, a parasite, Ureoplasma species, *Mycoplasma* species, *Chlamydia* species, or *Pneumocystis* species, wherein the subject is otherwise free of indications calling for treatment with gelsolin.

16. The method of claim 15, wherein the therapeutic agent is an anti-infective agent.

17. The method of claim 16, wherein the anti-infective agent is an anti-bacterial agent, an anti-viral agent, an anti-fungal agent, or anti-protozoal agent.

18. The method of claim 15, wherein the therapeutic agent is an antibiotic.

19. A method for treating a subject at risk of developing an infection comprising:
administering cytoplasmic gelsolin (cGSN) or plasma gelsolin (pGSN) to a subject at risk of developing an infection and in need of such a treatment in an effective amount to increase a blood level of gelsolin to prevent the infection that may be caused by a gram-positive bacterium, a gram-negative bacterium, an acid-fast *bacillus*, a spirochete, an actinomycete, a virus, a fungus, a parasite, Ureoplasma species, *Mycoplasma* species, *Chlamydia* species, or *Pneumocystis* species, wherein the gelsolin is administered prior to exposure of the subject to the infection, and wherein the subject is otherwise free of indications calling for treatment with gelsolin.

20. A method for treating an infection in a subject having a gram-positive bacterial infection comprising:
administering to a subject having a gram-positive bacterial infection and in need of an increased blood level of gelsolin for the treatment of the gram-positive bacterial infection an effective amount of cytoplasmic gelsolin (cGSN) or plasma gelsolin (pGSN) to increase the blood level of gelsolin to treat the gram-positive bacterial infection, wherein the cGSN or pGSN is administered to the subject at a time subsequent to exposure to the gram-positive bacterial infection.

21. The method of claim 20, further comprising administering a therapeutic agent to the subject with the gelsolin.

22. The method of claim 1, wherein the gram-positive bacterium is *Staphylococcus* species.

23. The method of claim 1, wherein the gram-positive bacterium is *Streptococcus* species.

24. The method of claim 1, wherein the gram-positive bacterium is *Bacillus anthracis*.

25. The method of claim 1, wherein the gram-positive bacterium is *Corynebacterium* species.

26. The method of claim 1, wherein the gram-positive bacterium is *Diphtheroids* species.

27. The method of claim 1, wherein the gram-positive bacterium is *Listeria* species.

28. The method of claim 1, wherein the gram-positive bacterium is *Erysipelothrix* species.

29. The method of claim 1, wherein the gram-positive bacterium is *Clostridium* species.

30. The method of claim 1, wherein the gelsolin is administered orally.

31. The method of claim 1, wherein the gelsolin is administered intravenously.

32. The method of claim 1, wherein the gelsolin is administered intramuscularly.

33. The method of claim 1, wherein the gelsolin is administered subcutaneously.

34. The method of claim 1, wherein the gelsolin is administered topically.

35. The method of claim 20, wherein the gelsolin is pGSN.

36. The method of claim 1, wherein the subject is otherwise free of indications calling for treatment with gelsolin.

37. The method of claim 10, wherein the subject is otherwise free of indications calling for treatment with gelsolin.

38. The method of claim 15, wherein the subject is otherwise free of indications calling for treatment with gelsolin.

39. The method of claim 20, wherein the subject is otherwise free of indications calling for treatment with gelsolin.

* * * * *